(12) United States Patent
Arzeno

(10) Patent No.: US 6,849,710 B1
(45) Date of Patent: *Feb. 1, 2005

(54) METHOD FOR THE SYNTHESIS OF ANALOGS OF PARATHYROID HORMONE AND PARATHYROID HORMONE RELATED PEPTIDE

(75) Inventor: Humberto Arzeno, Cupertino, CA (US)

(73) Assignee: F. Hoffmann-La Roche AG, Basle (CH)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/903,124

(22) Filed: Jul. 30, 1997

Related U.S. Application Data

(60) Provisional application No. 60/023,322, filed on Jul. 30, 1996.

(51) Int. Cl.[7] ............................. C07K 1/02; C07K 7/06; C07K 7/08; C07K 14/00
(52) U.S. Cl. ....................... 530/324; 530/327; 530/328; 530/333; 530/338; 530/339; 530/402
(58) Field of Search ................................ 530/333, 324, 530/402, 338, 339, 328, 327

(56) References Cited

U.S. PATENT DOCUMENTS

| | | | |
|---|---|---|---|
| 3,886,132 A | 5/1975 | Brewer et al. | 260/112.5 |
| 4,656,250 A | 4/1987 | Morita et al. | 530/324 |
| 5,589,452 A | * 12/1996 | Krstenansky et al. | 514/12 |

FOREIGN PATENT DOCUMENTS

| | | |
|---|---|---|
| EP | 0 490 806 A2 | 6/1992 |
| FR | 2 550 204 | 2/1985 |
| WO | WO 94/01460 | 1/1994 |
| WO | WO 95/02610 | 1/1995 |
| WO | WO 9603437 A1 | 2/1996 |

OTHER PUBLICATIONS

Lloyd–Williams, et al. "Convergent Solid–Phase Peptide Synthesis", Tehtrahedron, vol. 49, No. 48, pp. 11065–111333, 1993.*

Database CAPLUS on STN, No. 1980:495635; Takai et al., "A Solution Synthesis of Biologically Active Fragment (1–34) of Human Parathyroid Hormone According to the Sequence Proposed by Niall", Peptide Chemistry (1980), vol. Date 1979, 17th, pp. 187–192, 1980.*

C. Paul Bianchi, "Pharmacodynamics", Chem Abstracts 93:9, p. 1 (1980).

Takai et al., "A Solution Synthesis of a Biologically Active Fragment (1–34) of Human Parathyroid Hormone According to the Sequence Proposed by Niall", Peptide Chemistry 1979, pp. 187–192.

Funakoshi et al., "Studies on Peptides. CVIII.[1,2] Synthesis of the Protected Eicosapeptide Corresponding to Positions 19 to 38 of Human Parathyroid Hormone", Chem. Pharm. Bull. 30:5, pp. 1697–1705 (1982).

Funakoshi et al., "Studies on Peptides. CIX.[1,2] Synthesis of the Octatriacontapeptide Corresponding to Positions 1 to 38 of Human Parathyroid Hormone", Chem. Pharm. Bull. 30:5, pp. 1706–1717 (1982).

Kuroda et al., "Powerful solvent systems useful for synthesis of sparingly–soluble peptides in solution", Int. J. Peptide Protein Res. 40, 294–299 (1992).

Williams et al., "Convergent Solid–Phase Peptide Synthesis", Tetrahedron 49:48, pp. 11065–11133 (1993).

* cited by examiner

Primary Examiner—Christopher S. F. Low
Assistant Examiner—Anish Gupta
(74) Attorney, Agent, or Firm—Heller Ehrman White & McAuliffe LLP

(57) ABSTRACT

A fragment condensation process for the synthesis of analogs of parathyroid hormone (PTH) and parathyroid hormone related peptide (PTHrP), in which amino acid residues (22–31) form a synthetic amphipathic α-helix, is provided.

20 Claims, No Drawings

METHOD FOR THE SYNTHESIS OF ANALOGS OF PARATHYROID HORMONE AND PARATHYROID HORMONE RELATED PEPTIDE

This application claims priority from U.S. Provisional Application No. 60/023,322, filed Jul. 30, 1996.

BACKGROUND OF THE INVENTION a) Field of the Invention

This invention relates to a method for the synthesis of certain novel analogs of parathyroid hormone and parathyroid hormone related peptide useful for the treatment of osteoporosis.

b) Description of Related Art

Osteoporosis is the most common form of metabolic bone disease and may be considered the symptomatic, fracture stage of bone loss (osteopenia). Although osteoporosis may occur secondary to a number of underlying diseases, 90% of all cases appear to be idiopathic. Postmenopausal women are particularly at risk for idiopathic osteoporosis (postmeno-pausal or Type I osteoporosis). Another high risk group for idiopathic osteoporosis is the elderly of either sex (senile or Type II osteoporosis). Osteoporosis has also been related to corticosteroid use, immobilization or extended bed rest, alcoholism, diabetes, gonadotoxic chemotherapy, hyperprolactinemia, anorexia nervosa, primary and secondary amenorrhea, and oophorectomy.

In the various forms of osteoporosis, bone fractures, which are the result of bone loss that has reached the point of mechanical failure, frequently occur. Postmenopausal osteoporosis is characterized by fractures of the wrist and spine, while femoral neck fractures seem to be the dominant feature of senile osteoporosis.

The mechanism by which bone is lost in osteoporotics is believed to involve an imbalance in the process by which the skeleton renews itself. This process has been termed bone remodeling. It occurs in a series of discrete pockets of activity. These pockets appear spontaneously within the bone matrix on a given bone surface as a site of bone resorption. Osteoclasts (bone dissolving or resorbing cells) are responsible for the resorption of a portion of bone of generally constant dimension. This resorption process is followed by the appearance of osteoblasts (bone forming cells) which then refill with new bone the cavity left by the osteoclasts.

In a healthy adult subject, the rate at which osteoclasts and osteoblasts are formed is such that bone formation and bone resorption are in balance. However, in osteoporotics an imbalance in the bone remodeling process develops which results in bone being lost at a rate faster than it is being made. Although this imbalance occurs to some extent in most individuals as they age, it is much more severe and occurs at a younger age in postmenopausal osteoporotics or following oophorectomy.

Adachi, et al. in *Seminars in Arthritis and Rheumatism*, 22:6, 375–84 (June 1993) report that despite much conflicting data regarding the pathophysiology of corticosteroid induced osteoporosis, it is generally agreed that there is a relative decrease in bone formation and a relative increase in bone resorption. Bone loss with resulting fractures and osteonecrosis is a frequent consequence of corticosteroid therapy. There is evidence that bone loss occurs rapidly within the first 6 to 12 months of corticosteroid therapy; there also appears to be a close relationship between rate of bone loss and corticosteroid dose. Men are equally susceptible to the effects of corticosteroids. The estimated incidence of fractures and osteonecrosis ranges from 30 to 50%.

There have been many attempts to treat osteoporosis with the goal of either slowing further bone loss or, more desirably, producing a net gain in bone mass. Certain agents, such as estrogen and the bisphosphonates, appear to slow further bone loss in osteoporotics. Agents which slow bone loss, because of the different durations of bone resorption and formation, may appear to increase bone mass (on the order of 3 to 7%). However, this apparent increase is limited in time, not progressive, and is due to a decrease in "remodeling space." In addition, because of the close coupling between resorption and formation, treatments which impede bone resorption also ultimately impede bone formation.

It has been suggested that treatment with parathyroid hormone (PTH) would lead to both increased bone turnover and a positive calcium balance. However, human clinical trials have shown that any increase in trabecular bone is offset by a decrease in cortical bone, so that there is no net increase in total bone.

Hefti, et al. in *Clinical Science* 62, 389–396 (1982) have reported that daily subcutaneous doses of either bPTH(1–84) or hPTH(1–34) increased whole body calcium and ash weight of individual bones in both normal and osteoporotic adult female rats.

Liu, et al. in *J. Bone Miner. Res.* 6:10, 1071–1080 (1991) have noted that ovariectomy of adult female rats induced a 47% loss in the percentage of trabecular bone in the proximal tibial metaphysis, accompanied by a significant increase in the number of osteoblasts and trabecular osteoclasts. Daily subcutaneous injections of hPTH(1–34) completely reversed the loss of trabecular bone and resulted in amounts of trabecular bone exceeding that of sham operated controls. The number of osteoblasts increased and the number of osteoclasts decreased.

Hock et al. in *J. Bone Min. Res.* 7:1, 65–71 (1992) have reported that daily subcutaneous injections of hPTH(1–34) to healthy adult male rats for 12 days increased trabecular and cortical bone calcium and dry weight. Total bone mass, trabecular bone volume, trabecular thickness and number, and osteoblastic surfaces were increased.

The mammalian parathyroid hormones, e.g. human (hPTH), bovine (bPTH), and porcine (pPTH), are single polypeptide chains of 84 amino acid residues, with molecular weights of approximately 9500. Biological activity is associated with the N-terminal portion, with residues (1–34) apparently the minimum required.

The N-terminal segment of human PTH differs from the N-terminal segment of the bovine and porcine hormones by only three and two amino acid residues, respectively:

```
hPTH(1-34):
Ser Val Ser Glu Ile Gln Leu Met His Asn Leu Gly Lys His Leu (SEQ ID NO:1)
1             5                   10                  15
Asn Ser Met Glu Arg Val Glu Trp Leu Arg Lys Lys Leu Gln Asp
```

-continued

```
                  20              25             30
Val His Asn Phe;

bPTH(1-34):
Ala Val Ser Glu Ile Gln Phe Met His Asn Leu Gly Lys His Leu  (SEQ ID NO:2)
1               5                   10              15
Ser Ser Met Glu Arg Val Glu Trp Leu Arg Lys Lys Leu Gln Asp
                  20              25             30
Val His Asn Phe;

pPTH(1-34):
Ser Val Ser Glu Ile Gln Leu Met His Asn Leu Gly Lys His Leu  (SEQ ID NO:3)
1               5                   10              15
Ser Ser Leu Glu Arg Val Glu Trp Leu Arg Lys Lys Leu Gln Asp
                  20              25             30
Val His Asn Phe.
```

The primary function of PTH is to elicit the adaptive changes that serve to maintain a constant concentration of $Ca^{2+}$ in the extracellular fluid. PTH acts on the kidneys to increase tubular reabsorption of $Ca^{2+}$ from the urine, as well as stimulating the conversion of calcifediol to calcitriol, which is responsible for absorption of $Ca^{2+}$ from the intestines. One prominent effect is to promote the mobilization of $Ca^{2+}$ from bone. PTH acts on bone to increase the rate of resorption of $Ca^{2+}$ and phosphate. PTH stimulates the rate of bone resorption by osteoclasts, increases the rate of differentiation of mesenchymal cells to osteoclasts, and prolongs the half life of these latter cells. With prolonged action of PTH the number of bone forming osteoblasts is also increased; thus, the rate of bone turnover and remodeling is enhanced. However, individual osteoblasts appear to be less active than normal.

Rosenblatt, et al. in U.S. Pat. Nos. 4,423,037, 4,968,669 and 5,001,223 have disclosed PTH antagonists obtained by the deletion of the N-terminal (1–6) amino acids and the selective replacement of $Phe^7$, $Met^{8,18}$, and $Gly^{12}$. $Tyr^{34}$-$NH_2$ reportedly increased the activity and stability of these compounds.

Parathyroid hormone-related peptide (PTHrp), a 140+ amino acid protein, and fragments thereof, reproduce the major biological actions of PTH. PTHrp is elaborated by a number of human and animal tumors and other tissues and may play a role in hypercalcemia of malignancy. The sequence of hPTHrp (1–34) is as follows:

```
Ala Val Ser Glu His Gln Leu Leu His Asp Lys Gly Lys Ser Ile  (SEQ ID NO:4)
1               5                   10              15
Gln Asp Leu Arg Arg Arg Phe Phe Leu His His Leu Ile Ala Glu
                  20              25             30
Ile His Thr Ala.
```

The sequence homology between hPTH and hPTHrp is largely limited to the 13 N-terminal residues, 8 of which are identical; only 1 of 10 amino acids in the (25–34) receptor binding region of hPTH is conserved in hPTHrp. Conformational similarity may underlie the common activity. Cohen, et al. in *J. Biol. Chem.* 266:3, 1997–2004 (1991) have suggested that much of the sequence of PTH(1–34) and PTHrp(1–34), in particular regions (5–18) and (21–34), assumes an α-helical configuration, while noting that there is some question whether this configuration prevails for the carboxyl terminal end under physiological conditions. Such a secondary structure may be important for lipid interaction, receptor interaction, and/or structural stabilization.

We have synthesized analogs of PTH and of PTHrp with the objective of developing improved therapeutic agents for the restoration of bone mass in mammalian subjects, including those afflicted with osteoporosis.

The compounds of this invention are disclosed in U.S. Pat. No. 5,589,452, filed Jul. 14, 1992, issued Dec. 31, 1996, and in pending U.S. patent application Ser. No. 08/184,328, filed Jan. 18, 1994, and published in International Publication No. WO 94/01460 on Jan. 20, 1994, filed as International Application No. PCT/US93/06465 on Jul. 13, 1993. The foregoing are incorporated by reference herein. We now report an improved method for the synthesis of these compounds.

SUMMARY OF THE INVENTION

This invention provides an improved method for the synthesis of a synthetic polypeptide analog of parathyroid hormone (PTH) or parathyroid hormone related peptide (PTHrP), or salt thereof, in which amino acid residues (22–31) form an amphipathic α-helix, said residues (22–31) selected from (SEQ ID NOS: 85, 86, 26, 27, 28, 29, and 30), which method comprises a) independently synthesizing precursor peptide fragments of the polypeptide, by solution or solid phase techniques, b) condensing said fragments with each other to form the desired polypeptide product, and c) removing amino acid protecting groups.

In one embodiment this invention provides an improved method for the synthesis of a synthetic polypeptide analog of parathyroid hormone (PTH) or parathyroid hormone related peptide (PTHrP), or salt thereof, in which amino acid residues (22–31) form an amphipathic α-helix, said residues (22–31) selected from (SEQ ID NOS: 85, 86, 26, 27, 28, 29, and 30), which method comprises a) independently synthesizing precursor peptide fragments of the polypeptide on resin supports, b) cleaving the fragments of the polypeptide from their respective resin supports, c) sequentially condensing said fragments to form the desired polypeptide product, and d) removing amino acid protecting groups.

In a preferred embodiment this invention provides an improved method for the synthesis of a synthetic polypeptide analog of parathyroid hormone (PTH) or parathyroid hormone related peptide (PTHrP), or salt thereof, in which amino acid residues (22–31) form an amphipathic α-helix, said residues (22–31) selected from (SEQ ID NOS: 85, 86, 26, 27, 28, 29, and 30), which method comprises a) independently synthesizing precursor peptide fragments of the polypeptide on resin supports, b) cleaving all but the C-terminal fragment of the polypeptide from their respective resin supports, c) sequentially condensing said fragments with the resin bound C-terminal fragment to form the desired polypeptide product, and d) removing amino acid protecting groups and cleaving the polypeptide product from the resin support.

In a preferred embodiment the process is practiced with three precursor peptide fragments: an N-terminus fragment, a middle fragment, and a C-terminus fragment. In a more preferred embodiment, the fragments have a glutamic acid, glycine, or leucine residue at their C-termini when consistent with the sequence of the desired final polypeptide. In a most preferred embodiment the polypeptide product is prepared from three precursor peptide fragments, N-terminal, middle, and C-terminal, in which the N-terminal fragment has a Gly as its C-terminus, the middle peptide fragment has a Leu as its C-terminus, and the C-terminal fragment has a Leu as its N-terminus. In an alternative embodiment, the middle peptide fragment has a C-terminal Glu and the C-terminal fragment has an N-terminal Leu.

DETAILED DESCRIPTION OF THE INVENTION

Abbreviations and Definitions

The one- and three-letter abbreviations for the various common nucleotide bases and amino acids are as recommended in *Pure Appl. Chem.* 31, 639–645 (1972) and 40, 277–290 (1974) and the IUPAC-IUB Biochemical Nomenclature Commission and comply with 37 CFR §1.822 (55 FR 18245, May 1, 1990). The one- and three-letter abbreviations are as follows:

| Amino Acid Symbol | Three-letter Symbol | One-letter |
|---|---|---|
| Alanine | Ala | A |
| Argine | Arg | R |
| Asparagine | Asn | N |
| Aspartic Acid | Asp | D |
| Ans + Asp | Asx | B |
| Cysteine | Cys | C |
| Glutamine | Gln | Q |
| Glutamic Acid | Glu | E |
| Gln + Glu | Glx | Z |
| Glycine | Cly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |
| Other amino acid | Xaa | X |

The abbreviations represent L-amino acids unless otherwise designated as D- or D,L-. Certain amino acids, both natural and non-natural, are achiral, e.g. glycine. All peptide sequences are presented with the N-terminal amino acid on the left and the C-terminal amino acid on the right.

Further abbreviations for other amino acids and compounds used herein are:

| hSer | homoserine |
| hSerlac | homoserine lactone |
| Nle | norleucine |

"Physiologically active truncated analog of PTH or PTHrp" refers to a polypeptide having a sequence comprising less than the full complement of amino acids found in PTH or PTHrp which, however, elicits a similar physiological response. The truncated PTH or PTHrp need not be fully homologous with PTH or PTHrp to elicit a similar physiological response. PTH(1–34) and PTHrp(1–34) are preferred, but not exclusive, representatives of this group.

"Amphipathic α-helix" refers to the secondary structure exhibited by certain polypeptides in which the amino acids assume an α-helical configuration having opposing polar and nonpolar faces oriented along the long axis of the helix. The possibility of α-helical structure in the polypeptide of interest may be explored to some extent by the construction of a "Schiffer-Edmundson wheel" (M. Schiffer and A. B. Edmundson, *Biophys. J.* 7, 121 (1967)), of the appropriate pitch and noting the segregation of the hydrophilic and lipophilic residues on opposite faces of the cylinder circumscribing the helix. Alternatively, empirical evidence, such as circular dichroism or x-ray diffraction data, may be available indicating the presence of an α-helical region in a given polypeptide. An ideal α-helix has 3.6 amino acid residues per turn with adjacent side chains separated by 100° of arc. Eisenberg et al. in *Nature* 299:371–374 (1982) and *Proc. Nat. Acad. Sci. USA* 81:140–144 (1984) have combined a hydrophobicity scale with the helical wheel to quantify the concept of amphipathic helices. The mean hydrophobic moment is defined as the vector sum of the hydrophobicities of the component amino acids making up the helix. The following hydrophobicities for the amino acids are those reported by Eisenberg (1984) as the "consensus" scale:

Ile 0.73; Phe 0.61; Val 0.54; Leu 0.53; Trp 0.37;
Met 0.26 Ala 0.25; Gly 0.16; Cys 0.04; Tyr 0.02;
Pro −0.07; Thr −0.18; Ser −0.26; His −0.40; Glu −0.62;
Asn −0.64; Gln −0.69; Asp −0.72; Lys −1.10; Arg −1.76.

The hydrophobic moment, $\mu_H$, for an ideal α-helix having 3.6 residues per turn (or a 100° arc (=360°/3.6) between side chains), may be calculated from:

$$\mu_H = [(\Sigma H_N \sin \delta(N-1))^2 + (\Sigma H_N \cos \delta(N-1))^2]^{1/2},$$

where $H_N$ is the hydrophobicity value of the $N^{th}$ amino acid and the sums are taken over the N amino acids in the sequence with periodicity $\delta = 100°$. The hydrophobic moment may be expressed as the mean hydrophobic moment per residue by dividing $\mu_H$ by N to obtain $<\mu_H>$. A value of $<\mu_H>$ at 100°±20° of about 0.20 or greater is suggestive of amphipathic helix formation. The $<\mu_H>$ values at 100° for hPTHrp (22–31) and hPTH (22–31) are 0.19 and 0.37, respectively.

Cornett, et al., in *J. Mol. Biol.*, 195:659–685 (1987) have further extended the study of amphipathic α-helices by introducing the "amphipathic index" as a predictor of amphipathicity. They concluded that approximately half of all known α-helices are amphipathic, and that the dominant frequency is 97.5° rather than 100°, with the number of residues per turn being closer to 3.7 than 3.6. While such refinements are scientifically interesting, the basic approach of Eisenberg, et al. is sufficient to classify a given sequence as amphipathic, particularly when one is designing a sequence ab initio to form an amphipathic α-helix.

A substitute amphipathic α-helical amino acid sequence may lack homology with the sequence of a given segment of a naturally occurring polypeptide but elicits a similar secondary structure, i.e. an α-helix having opposing polar and nonpolar faces, in the physiological environment. Replacement of the naturally occurring amino acid sequence with an alternative sequence may beneficially affect the physiological activity, stability, or other properties of the altered parent polypeptide. Guidance as to the design and election of such sequences is provided in J. L. Krstenansky, et al., *FEBS Letters* 242:2, 409–413 (1989), and J. P. Segrest, et al. *Proteins: Structure, Function, and Genetics* 8:103–117 (1990) among others.

A convenient method for determining if a sequence is sufficiently amphipathic to be a sequence of this invention is to calculate the mean hydrophobic moment, as defined above. If the peak mean moment per residue at 100±20° exceeds about 0.20, then the sequence will form an amphipathic helix and is a sequence of this invention.

For example, the mean hydrophobic moment per residue at 100° for (SEQ ID NO: 26), Xaa=Glu, is calculated as follows:

| A.A. | $H_N$ | δ (N-1) | H sin δ(N-1) | H cos δ(N-1) |
|------|-------|---------|--------------|--------------|
| E | −.62 | 0 | 0 | −.62 |
| L | .53 | 100 | .52 | −.17 |
| L | .53 | 300 | −.18 | −.50 |
| E | −.62 | 300 | .34 | −.31 |
| K | −1.1 | 400 | −.70 | −.85 |
| L | .53 | 500 | .34 | −.41 |
| L | .53 | 600 | −.46 | −.27 |
| E | −.62 | >700 | .21 | −.58 |
| K | −1.1 | 800 | −1.08 | −.19 |

-continued

| A.A. | $H_N$ | δ (N-1) | H sin δ(N-1) | H cos δ(N-1) |
|------|-------|---------|--------------|--------------|
| L | .53 | 900 | 0 | −.53 |
| | | | ρ = 0.81 | ρ = 4.43 |

$\mu_H = [(0.81)^2 + (-4.43)^2]^{1/2} = 4.50$
$<\mu_H> = 4.50/10 = 0.45$

For this sequence, the mean peak hydrophobic moment occurs at 92° and has a value of 0.48.

PREFERRED EMBODIMENTS

In one aspect, this invention provides processes for the synthesis of PTH, PTHrP, and the physiologically active analogs of PTH and PTHrp, or salts thereof, in which amino acid residues (22–31) form an amphipathic α-helix, the sequence of said residues (22–31) selected from:

a) Xaa$^1$ Xaa$^2$ Leu Xaa$^4$ Xaa$^5$ Leu Xaa$^7$ Xaa$^8$ Xaa$^9$ Xaa$^{10}$ wherein
   1          5                    10
   Xaa$^1$ and Xaa$^4$ are independently Glu, Glu(OCH$_3$), His, or Phe; Xaa$^2$ is Leu or Phe;
   Xaa$^5$ is Lys or His;
   Xaa$^7$ and Xaa$^{10}$ are independently Leu or Ile;
   Xaa$^8$ is Ala, Arg, or Glu; and
   Xaa$^9$ is Lys or Glu (SEQ ID NO: 85);
   preferably Glu Leu Leu Glu Lys Leu Leu Xaa Lys Leu wherein
                        5              10
   Xaa is Glu or Arg (SEQ ID NO:26);

b) Xaa$^1$ Xaa$^2$Leu Xaa$^4$ Arg Leu Leu Xaa$^8$ Arg Leu wherein
   1          5                    10
   Xaa$^1$ and Xaa$^4$ are independently Glu, Glu(OCH$_3$), His, or Phe; Xaa$^2$ is Leu or Phe;
   Xaa$^8$ is Glu or Lys (SEQ ID NO:86);
   preferably, Glu Leu Leu Glu Arg Leu Leu Xaa Arg Leu
                1              5                    10
   wherein Xaa is Glu or Lys (SEQ ID NO:27);

c) Ala Leu Ala Glu Ala Leu Ala Glu Ala Leu (SEQ ID NO:28);
   1              5              10 d) Ser Leu Leu Ser Ser Leu Leu Ser Ser Leu (SEQ ID NO:29);
   1              5              10 e) Ala Phe Tyr Asp Lys Val Ala Glu Lys Leu (SEQ ID NO:30).
   1              5              10

In another aspect, this invention provides processes for the synthesis of PTH, PTHrP, and the physiologically active analogs of PTH and PTHrp, or salts thereof, of the formula:

Xaa$^1$ Xaa$^2$ Xaa$^3$ Xaa$^4$ Xaa$^5$ Xaa$^6$ Xaa$^7$ Leu His Asp Xaa$^{11}$ Gly Xaa$^{13}$ Ser Ile Gln Asp Leu Xaa$^{19}$ Xaa$^{20}$ Xaa$^{21}$ Xaa$^{22-31}$ Xaa$^{32}$ Xaa$^{33}$ Xaa$^{34}$ Xaa$^{35}$ Xaa$^{36}$ Xaa$^{37}$ Xaa$^{38}$

Term, wherein:
Xaa$^1$ is absent or is Ala;
Xaa$^2$ is absent or is Val;
Xaa$^3$ is absent or is Ser;
Xaa$^4$ is absent or is Glu or Glu(OCH$_3$);
Xaa$^5$ is absent or is His or Ala;
Xaa$^6$ is absent or is Gln;
Xaa$^7$ is absent or is Leu;
Xaa$^8$ is Lys, Arg, or Leu;
Xaa$^{13}$ is Lys, Arg, Tyr, Cys, Leu, Cys(CH$_2$CONH(CH$_2$)$_2$NH(biotinyl)), Lys(7-dimethylamino-2-oxo-2H-1-benxopyran-4-acetyl), or Lys(dihydrocinnamoyl);
Xaa$^{20}$ is Arg or Leu;
Xaa$^{19}$ and Xaa$^{21}$ are independently Lys, Ala, or Arg;
Xaa$^{22-31}$ is selected from (SEQ ID NOS:26, 27, 28, 29, or 30); Xaa$^{32}$ is His, Pro, or Lys;
Xaa$^{33}$ is absent, or is Pro, Thr, Glu, or Ala;

Xaa$^{34}$ is absent, or is Pro, Arg, Met, Ala, hSer, hSer lactone, Tyr, or Leu;

Xaa$^{35}$ is absent or is Pro, Glu, Ser, Ala, or Gly;

Xaa$^{36}$ is absent or is Ala, Arg, or Ile;

Xaa$^{37}$ is absent or is Arg, Trp, or 3-(-2-naphthyl)-L-alanine;

Xaa$^{38}$ is absent or is Ala or hSer or Xaa$^{38-42}$ is Thr Arg Ser Ala Trp;

and Term is

OR or NR$_2$ where each R is independently H, (C$_1$–C$_4$) alkyl or phenyl(C$_1$–C$_4$)alkyl; and the pharmaceutically acceptable salts thereof.

In yet another aspect this invention includes processes for the synthesis of polypeptide analogs of the physiologically active truncated homolog hPTHrp(1–34), as shown in Formula (I):

Ala Val Ser Glu Xaa$^5$ Gln Leu Leu His Asp Xaa$^{11}$ Gly Xaa$^{13}$ Ser Ile Gln Asp Leu Xaa$^{19}$ Arg Xaa$^{21}$ Xaa$^{22-31}$ Xaa$^{32}$ Xaa$^{33}$ Xaa$^{34}$

Term, wherein:

Xaa$^5$ is His or Ala;

Xaa$^{11}$ and Xaa$^{13}$ are independently Lys, Arg, or Leu;

Xaa$^{19}$ and Xaa$^{21}$ are independently Ala or Arg;

Xaa$^{22-31}$ is selected from:

a)  Glu Leu Leu Glu Lys Leu Leu Xaa Lys Leu
    1             5                    10
    wherein
    Xaa is Glu or Arg (SEQ ID NO:26);

b)  Glu Leu Leu Glu Arg Leu Leu Xaa Arg Leu
    1             5                    10
    wherein
    Xaa is Glu or Lys (SEQ ID NO:27);

c)  Ala Leu Ala Glu Ala Leu Ala Glu Ala Leu
    1             5                    10
    (SEQ ID NO:28);

d)  Ser Leu Leu Ser Ser Leu Leu Ser Ser Leu
    1             5                    10
    (SEQ ID NO:29);

e)  Ala Phe Tyr Asp Lys Val Ala Glu Lys Leu
    1             5                    10
    (SEQ ID NO:30);

Xaa$^{32}$ is His or Lys;

Xaa$^{33}$ is Thr, Glu, or Ala;

Xaa$^{34}$ is Ala, hSer, Tyr, or Leu;

and Term is

Gly Arg Arg, lactone, OH or NR$_2$, where each R is H or (C$_1$–C$_4$) alkyl; and their pharmaceutically acceptable salts. (Formula I)

A more specific aspect of the invention includes the synthesis of those polypeptides of Formula (I) wherein Xaa$^{22-31}$ is (SEQ ID NO:26), for which $<\mu_H>$ at 100° exceeds 0.45. A still more specific aspect of the invention includes those Formula (I) polypeptides wherein Xaa$^{22-31}$ is (SEQ ID NO:26); Xaa$^{11}$ and Xaa$^{13}$ are both Lys; and Xaa$^{19}$ and Xaa$^{21}$ are both Arg. Representative polypeptides which may be prepared by the processes disclosed herein include, but are not limited to:

```
Ala Val Ser Glu His Gln Leu Leu His Asp Lys Gly Lys Ser Ile  (SEQ ID NO:5)
1               5                   10                  15
Gln Asp Leu Arg Arg Arg Glu Leu Leu Glu Lys Leu Leu Arg Lys
                20                  25                  30
Leu His Thr Ala OH;

Ala Val Ser Glu His Gln Leu Leu His Asp Lys Gly Lys Ser Ile  (SEQ ID NO:6)
1               5                   10                  15
Gln Asp Leu Arg Arg Arg Glu Leu Leu Glu Lys Leu Leu Glu Lys
                20                  25                  30
Leu His Thr Ala OH;

Ala Val Ser Glu His Gln Leu Leu His Asp Lys Gly Lys Ser Ile  (SEQ ID NO:7)
1               5                   10                  15
Gln Asp Leu Arg Arg Arg Glu Leu Leu Glu Lys Leu Leu Glu Lys
                20                  25                  30
Leu His Thr Ala NH$_2$ ;

Ala Val Ser Glu His Gln Leu Leu His Asp Lys Gly Lys Ser Ile  (SEQ ID NO:8)
1               5                   10                  15
Gln Asp Leu Arg Arg Arg Glu Leu Leu Glu Lys Leu Leu Glu Lys
                20                  25                  30
Leu His Thr hSer NH$_2$ ;

Ala Val Ser Glu His Gln Leu Leu His Asp Lys Gly Lys Ser Ile  (SEQ ID NO:9)
1               5                   10                  15
Gln Asp Leu Arg Arg Arg Glu Leu Leu Glu Lys Leu Leu Glu Lys
                20                  25                  30
Leu His Thr hSerlac;

Ala Val Ser Glu His Gln Leu Leu His Asp Lys Gly Lys Ser Ile  (SEQ ID NO:10)
1               5                   10                  15
Gln Asp Leu Arg Arg Arg Glu Leu Leu Glu Lys Leu Leu Glu Lys
                20                  25                  30
Leu His Thr Ala Gly Arg Arg OH; and
                35
```

```
Ala Val Ser Glu His Gln Leu Leu His Asp Lys Gly Lys Ser Ile  (SEQ ID NO:11)
1               5                   10                  15
Gln Asp Leu Arg Arg Arg Glu Leu Leu Glu Lys Leu Leu Glu Lys
                20                  25                  30
Leu Lys Glu Leu NH2 .
```

Another aspect of this invention includes the synthesis of those polypeptides of Formula (I) wherein $Xaa^{22\text{-}31}$ is (SEQ ID NO:26); $Xaa^{11}$ and $Xaa^{13}$ are both Lys; and one of $Xaa^{19}$ and $Xaa^{21}$ is Arg and the other is Ala. Representative poly-peptides of this subgenus which may be prepared by the processes disclosed herein include, but are not limited to:

In another aspect this invention includes the synthesis of polypeptides of Formula (I) wherein $Xaa^{22\text{-}31}$ is (SEQ ID NO:28), for which $<\mu_H>$ at 100° is about 0.25. Repre/sentative polypeptides of this subgenus which may be prepared by the processes of this invention include, but are not limited to:

```
Ala Val Ser Glu His Gln Leu Leu His Asp Lys Gly Lys Ser Ile  (SEQ ID NO:12)
1               5                   10                  15
Gln Asp Leu Ala Arg Arg Glu Leu Leu Glu Lys Leu Leu Glu Lys
                20                  25                  30
Leu His Thr Ala NH2 and Ala Val Ser Glu His Gln Leu Leu His Asp Lys Gly Lys Ser Ile  (SEQ ID NO:13)
1               5                   10                  15
Gln Asp Leu Arg Ala Arg Glu Leu Leu Glu Lys Leu Leu Glu Lys
                20                  25                  30
Leu His Thr Ala NH2 .
```

In another aspect this invention includes the synthesis of those polypeptides of Formula (I) wherein $Xaa^{22\text{-}31}$ is (SEQ ID NO:26); one of $Xaa^{11}$ and $Xaa^{13}$ is Leu and the other is Lys; and $Xaa^{19}$ and $Xaa^{21}$ are both Arg. Representative poly-peptides of this subgenus which may be prepared by the processes of this invention include, but are not limited to:

```
Ala Val Ser Glu Ala Gln Leu Leu His Asp Leu Gly Lys Ser Ile  (SEQ ID NO:14)
1               5                   10                  15
Gln Asp Leu Arg Arg Arg Glu Leu Leu Glu Lys Leu Leu Glu Lys
                20                  25                  30
Leu His Ala Leu OH.
```

In another aspect this invention includes the synthesis of those polypeptides of Formula (I) wherein $Xaa^{22\text{-}31}$ is (SEQ ID NO:27), for which $<\mu_H>$ at 100° exceeds 0.50. A further aspect of this invention includes the synthesis of those Formula (I) polypeptides wherein $Xaa^{22\text{-}31}$ is (SEQ ID NO:27); $Xaa^{11}$ and $Xaa^{13}$ are both Lys or both Arg; and $Xaa^{19}$ and $Xaa^{21}$ are both Arg. Representative polypeptides of this subgenus which may be prepared by the processes of this invention include, but are not limited to:

```
Ala Val Ser Glu His Gln Leu Leu His Asp Lys Gly Lys Ser Ile  (SEQ ID NO:15)
1               5                   10                  15
Gln Asp Leu Arg Arg Arg Glu Leu Leu Glu Arg Leu Leu Glu Arg
                20                  25                  30
Leu His Thr Ala OH;

Ala Val Ser Glu His Gln Leu Leu His Asp Arg Gly Arg Ser Ile  (SEQ ID NO:16)
1               5                   10                  15
Gln Asp Leu Arg Arg Arg Glu Leu Leu Glu Arg Leu Leu Glu Arg
                20                  25                  30
Leu His Thr Ala OH;

Ala Val Ser Glu His Gln Leu Leu His Asp Arg Gly Arg Ser Ile  (SEQ ID NO:17)
1               5                   10                  15
Gln Asp Leu Arg Arg Arg Glu Leu Leu Glu Arg Leu Leu Lys Arg
                20                  25                  30
Leu His Thr Ala OH;
```

```
Ala Val Ser Glu His Gln Leu Leu His Asp Lys Gly Lys Ser Ile  (SEQ ID NO:20)
1             5                  10                 15
Gln Asp Leu Arg Arg Arg Ala Leu Ala Glu Ala Leu Ala Glu Ala
                20              25                 30
Leu His Thr Ala NH₂ .
```

In another aspect this invention includes the synthesis of polypeptides of Formula (I) wherein Xaa$^{22\text{-}31}$ is (SEQ ID NO:29), for which $<u_H>$ at 100° is about 0.28. Representative polypeptides of this subgenus which may be prepared by the processes of this invention include, but are not limited to:

```
Ala Val Ser Glu His Gln Leu Leu His Asp Lys Gly Lys Ser Ile  (SEQ ID NO:21)
1             5                  10                 15
Gln Asp Leu Arg Arg Arg Ser Leu Leu Ser Ser Leu Leu Ser Ser
                20              25                 30
Leu His Thr Ala NH₂ .
```

In another aspect this invention includes the synthesis of polypeptides of Formula (I) wherein Xaa$^{22\text{-}31}$ is (SEQ ID NO:30), for which $<u_H>$ at 100° is about 0.29. Representative polypeptides of this subgenus which may be synthesized by the processes of this invention include, but are not limited to:

```
Ala Val Ser Glu His Gln Leu Leu His Asp Lys Gly Lys Ser Ile  (SEQ ID NO:22)
1             5                  10                 15
Gln Asp Leu Arg Arg Arg Ala Phe Tyr Asp Lys Val Ala Glu Lys
                20              25                 30
Leu His Thr Ala NH₂ .
```

Still another aspect of this invention includes the synthesis of polypeptide analogs of the physiologically active homologs of bPTH(1–34), as shown in Formula (II):

```
Ala Val Ser Glu Ile Gln Phe Nle His Asn Leu Gly Lys His Leu  (SEQ ID NO:23)
1             5                  10                 15
Ser Ser Nle Glu Arg Val Glu Leu Leu Glu Lys Leu Leu Glu Lys
                20              25                 30
Leu His Asn Tyr NH₂ and Ala Val Ser Glu Ile Gln Phe Nle His Asn Leu Gly Lys His Leu  (SEQ ID NO:24)
1             5                  10                 15
Ser Ser Nle Arg Arg Arg Glu Leu Leu Glu Lys Leu Leu Glu Lys
                20              25                 30
Leu His Asn Tyr NH₂ .
```

Xaa$^1$ Val Ser Glu Ile Gln Xaa$^7$ Xaa$^8$ His Asn Leu Gly Lys His Leu Xaa$^{16}$ Ser Xaa$^{18}$ Xaa$^{19}$ Arg Xaa$^{21}$ Xaa$^{22\text{-}31}$ His Asn Xaa$^{34}$ Term, wherein:

Xaa$^1$ is Ser or Ala;

Xaa$^7$ is Leu or Phe;

Xaa$^8$ is Met or Nle;

Xaa$^{16}$ is Asn or Ser;

Xaa$^{18}$ is Leu, Met, or Nle;

Xaa$^{19}$ is Glu or Arg;

Xaa$^{21}$ is Val or Arg;

Xaa$^{22\text{-}31}$ is selected from (SEQ ID NO:26, 27, 28, 29, and 30); Xaa$^{34}$ is Phe or Tyr;

Term is OH or NR$_2$, where each R is H or (C$_1$–C$_4$)alkyl; and the pharmaceutically acceptable salts thereof.

Representative polypeptides which may be synthesized by the processes of this invention include, but are not limited to:

In still another aspect of this invention, processes for the synthesis of analogs of PTH and PTHrP having less than 34 amino acids are provided. These compounds are of general formula:

Ala Val Ser Glu Xaa$^5$ Gln Leu Leu His Asp Xaa$^{11}$ Gly Xaa$^{13}$ Ser Ile Gln Asp Leu Xaa$^{19}$ Arg Xaa$^{21}$ Xaa$^{22\text{-}31}$ Xaa$^{32}$ Xaa$^{33}$ Xaa$^{34}$ Term, Representative polypeptides which may be prepared by the processes of this invention include, but are not limited to:

Compound 41: AVSEHQLLHD KGKSIQDLRR RELLEKLLEK LHP-NH$_2$ (SEQ ID NO:55)

```
Ala Val Ser Glu His Gln Leu Leu His Asp Lys Gly Lys Ser Ile  (SEQ ID NO:55)
1             5                   10                      15
Gln Asp Leu Arg Arg Arg Glu Leu Leu Glu Lys Leu Leu Glu Lys
                20                  25                  30
Leu His Pro NH₂ .
```

Compound 42: AVSEHQLLHD KGKSIQDLRR RELLEKLLEK
        LP-NH₂                         (SEQ ID NO:56)

```
Ala Val Ser Glu His Gln Leu Leu His Asp Lys Gly Lys Ser Ile  (SEQ ID NO:56)
1             5                   10                      15
Gln Asp Leu Arg Arg Arg Glu Leu Leu Glu Lys Leu Leu Glu Lys
                20                  25                  30
Leu Pro NH₂ .
```

The skilled artisan will appreciate that numerous permutations of the polypeptide analogs may be synthesized which will possess the desirable attributes of those described herein provided that an amino acid sequence having a mean hydrophobic moment per residue at 100±20° greater than about 0.20 is inserted at positions (22–31).

Synthesis of the Polypeptides

The polypeptide fragments of the instant invention may be synthesized by methods such as those set forth by G. Barany, R. B. Merrifield in *The Peptides*, E. Gross and J. Meienhofer eds., Academic Press, New York (1979), Vol. 2, pp. 1–284; J. M. Stewart and J. D. Young, *Solid Phase Peptide Synthesis*, 2nd ed., Pierce Chemical Co., Rockford, Ill. (1984) and J. Meienhofer, *Hormonal Proteins and Peptides*, Vol. 2, Academic Press, New York, (1973) for solid phase synthesis and E. Schroder and K. Lubke, *The Peptides*, Vol. 1, Academic Press, New York, (1965) for solution synthesis. In general, these methods involve the sequential addition of protected amino acids to a growing peptide chain. Normally, either the amino or carboxyl group of the first amino acid and any reactive side chain group are protected. This protected amino acid is then either attached to an inert solid support, or utilized in solution, and the next amino acid in the sequence, also suitably protected is added under conditions amenable to formation of the amide linkage. After all the desired amino acids have been linked in the proper sequence, protecting groups and any solid support are removed to afford the crude polypeptide. The polypeptide is desalted and purified, preferably chromatographically, to yield the final product.

In the practice of this invention, the precursor peptide fragments may be prepared by either solution or solid phase techniques, or any combination thereof. For example, some of the fragments may be prepared in solution, and then condensed to a resin bound C-terminal fragment, or the fragments may each be prepared by a solid phase method, freed from the resin, and condensed in solution, or a mixed protocol of solution and solid phase syntheses may be employed.

A preferred method of preparing the PTH and PTHrP analogs of this invention, having fewer than about forty amino acids, involves solid phase fragment condensation peptide synthesis. In this method the ultimate product results from the condensation of several peptide precursor fragments. Depending upon the preference of the skilled worker, any combination of fragments may be used. For example, a 34 amino acid: product may be prepared-from two 17 amino acid peptide precursor fragments, three peptide precursor fragments, of varying lengths, four precursor fragments, etc. See P. LLoyd-Williams et al., "Convergent Solid Phase Peptide Synthesis," in *Tetrahedron*, 49:11065–11133 (1993) for illustrative discussion.

Generally, α-amino ($N^\alpha$) functions and any reactive side chains are protected by acid- or base-sensitive groups. The protecting group should be stable to the conditions of peptide linkage formation, while being readily removable without affecting the extant polypeptide chain. Suitable α-amino protecting groups include, but are not limited to t-butoxycarbonyl (Boc), benzyloxycarbonyl (Cbz), o-chlorobenzyloxycarbonyl, biphenylisopropyloxycarbonyl, t-amyloxycarbonyl (Amoc), isobornyloxycarbonyl, α,α-dimethyl-3,5-dimethoxybenzyloxycarbonyl, o-nitrophenylsulfenyl, 2-cyano-t-butoxycarbonyl, preferably 9-fluorenylmethoxycarbonyl (Fmoc). Suitable side chain protecting groups include, but are not limited to: acetyl, benzyl (Bzl), benzyloxymethyl (Bom), t-butyl, cyclohexyl, o-bromobenzyloxycarbonyl, t-butyldimethylsilyl, 2-chlorobenzyl (Cl-z), 2,6-dichlorobenzyl, 2,4-dinitrophenyl, cyclopentyl, isopropyl, pivalyl, tetrahydropyran-2-yl, tosyl (Tos), trimethylsilyl, methyltrityl, mesitylene sulfonyl (Mts), 4-methoxy-2,3,6-trimethylbenzenesulfonyl (Mtr), 2,2,4,6,7-pentamethyldihydrobenzofuran-5-sulfonyl (Pbf), 2,2,5,7,8-pentamethylchroman-6-sulfonyl (Pmc), and trityl (Trt).

In solid phase synthesis, the C-terminal amino acid is first attached to a suitable resin support. Suitable resin supports are those materials which are inert to the reagents and reaction conditions of the stepwise condensation and deprotection reactions, as well as being insoluble in the media used. Examples of commercially available resins include styrene/divinylbenzene resins modified with a reactive group, e.g., chloromethylated co-poly(styrene-divinylbenzene), hydroxymethylated co-poly(styrene-divinylbenzene), and benzylated, hydroxymethylated phenylacetamidomethyl (PAM) resins. To prepare acid terminal peptides, Wang resin may be used. A preferred resin is p-methylbenzhydrylamino-co-poly(styrene-divinylbenzene) resin (MBHA).

In the preferred embodiment, all fragments except the C-terminus fragment are prepared on an acid sensitive resin such as Sasrin (2-methoxy-4-alkoxybenzylalcohol) or 4-hydroxymethyl-3-methoxyphenoxybutyric acid 4-methylbenzhydrylamine (HMPB-MBHA). HMPA-MBHA, HMPB-BHA and HMPA-BHA resins are also suitable for the carboxy terminated peptides. The C-terminal fragment is prepared using a Knorr handle-MBHA resin. Sieber amide resins, Rink linker-MBHA or BHA resins, and Ramage linker-MBHA or BHA resins are all suitable for amide terminated peptides. These resins are commercially available with the first amino acid already bound or the first amino acid may be attached to the linker. The HMPB-MBHA and Knorr handle resins may be prepared as described in Examples 1, 2, and 3 below from MBHA resin. The successive coupling of the remaining protected amino acids may be carried out by methods well known in the art. Each protected amino acid is preferably introduced in approximately 1.5 to 2.5 fold molar excess and the coupling carried out in an inert, nonaqueous, polar solvent such as N-methyl pyrrolidinone (NMP), dichloromethane, dimethylformamide (DMF), dimethyl sulfoxide (DMSO), or mixtures thereof, preferably at ambient temperature. Representative coupling agents are N,N'-dicyclohexyl-carbodiimide (DCC), N,N'-diisopropylcarbodiimide (DIC) or other carbodiimide, either alone or in the presence of 1-hydroxybenzotriazole (HOBt), O-acyl ureas, benzotriazol-1-yl-oxytris(pyrrolidino)phosphonium hexafluorophosphate (PyBop), N-hydroxysuccinimide, other N-hydroxyimides, or oximes. Alternatively, protected amino acid active esters (e.g. p-nitrophenyl, pentafluorophenyl and the like) or symmetrical anhydrides may be used.

Successive coupling of Fmoc-protected amino acids is conducted using a solution of a secondary amine, such as pyridine, to remove the Fmoc group. The peptide resin may be checked for completed coupling by the Kaiser test after each coupling step.

At the end of the solid phase synthesis the fully protected peptide is removed from the resin using conditions which do not induce premature deprotection of side chain protecting groups. The peptides may be cleaved by saponification or transesterification or a mildly acidic deprotection regimen, employing for example 1% trifluoroacetic acid (TFA). The protected peptide may be purified by silica gel chromatography.

The solution may be desalted (e.g. with BioRad AG-3® anion exchange resin) and the peptide purified by a sequence of chromatographic steps employing any or all of the following types: hydrophobic adsorption chromatography on underivatized co-poly(styrene-divinylbenzene), e.g. Amberlite® XAD; silica gel adsorption chromatography; cation exchange chromatography on carboxymethylcellulose; partition chromatography, e.g. on Sephadex® G-25; countercurrent distribution; or reverse phase high performance liquid chromatography (HPLC), especially cation exchange and reverse-phase HPLC on octyl- or octadecyl-silylsilica (ODS) bonded phase column packing.

In one embodiment of the multi-fragment synthesis, the middle and N-terminal fragments are isolated and successively condensed to the C-terminal fragment. The polypeptide product is deprotected and cleaved from the resin, and further purified. The purification sequence is generally a comprehensive series of chromatographic separations. HPLC analysis determines the sequence and choice of purification. A typical sequence involves cation exchange, reverse phase HPLC, and reverse phase concentration column. The final solution is subjected to lyophilization and the drug product stored in amber bottles.

The following specific Examples are intended to illustrate the synthesis of representative compounds of the invention and should not be construed as limiting the scope of the claims. The protected amino acids were obtained from Genzyme (Cambridge, Mass.), Propeptide (Princeton, N.J.), or Synthetec (Albany, Oreg.).

The polypeptide of SEQ ID NO:7, a 34-amino acid peptide, AVSEHQLLHDKGKSIQDLRRRELLEKLLEKLHTA-NH$_2$, was prepared using a three-fragment condensation procedure. The N-terminus fragment consisted of amino acids 1 to 12, the middle fragment amino acids 13 to 23, and the C-terminus fragment amino acids 24 to 34. Each fragment was prepared by the solid phase method on a Vega 296 Automated Peptide Synthesizer. The automated mode was used for cleavage of the $N^\alpha$-protecting groups and for washes after coupling. Coupling reagents and solvents were added manually to the reaction vessel in the coupling step. The middle and N-terminus fragments were purified by HPLC and successively condensed to the C-terminus fragment. The final polypeptide was deprotected, cleaved from the resin, and purified.

EXAMPLE 1

Preparation of the N-Terminus Fragment

The N-terminus fragment, consisting of amino acids 1 to 12, AVSEHQLLHDKG, was prepared on a 250 mmole scale on the acid sensitive resin, 4-hydroxymethyl-3-methoxyphenoxy-butyric acid 4-methylbenzhydrylamine (HMPB-MBHA). This resin was prepared from MBHA resin (Novabiochem) as follows:

| STEP | EVENT | TIME (MINS) | REPETITIONS |
|------|-------|-------------|-------------|
| 1. | CH2C12/DMF (1/1) wash | 60 | 1 |
| 2. | 10% Et$_3$N in CH$_2$Cl$_2$ | 5 | 2 |
| 3. | CH$_2$Cl$_2$/DMF (1/1) | 5 | 3 |
| 4. | HMPB linker (1.15 eqs)/ PyBOP/DIPEA in CH$_2$Cl$_2$/DMF(1/1) | 300 @ 40 C. 500 @ RT | 1 |
| 5. | CH$_2$Cl$_2$ wash | 1.5 | 2 |
| 6. | DMF wash | 1.5 | 2 |
| 7. | CH$_2$Cl$_2$ wash | 1.5 | 1 |
| 8. | i-PrOH wash | 1.5 | 2 |
| 9. | CH$_2$Cl$_2$ wash | 1.5 | 3 |

After at least one DMF/CH$_2$Cl$_2$ wash, coupling of the first amino acid ($^{12}$Gly) was carried out using Fmoc-GlyOH (1.5–2.2 eqs.), DIC (1.5–2.2 eqs.), and DMAP (0.05 eq.) for about 15 hours at room temperature in DMF/CH$_2$Cl$_2$ (1/1), using the following protocol:

| STEP | EVENT | TIME (MINS) | REPETITIONS |
|------|-------|-------------|-------------|
| 1. | DMF/CH$_2$Cl$_2$ (1/1) | 60 | 1 |
| 2. | Fmoc-X-OH (2 eq.)/ DIC-DMAP (0.05 eq.) in CH$_2$Cl$_2$/DMF (1/1) | 900 | 1 |
| 3. | CH$_2$Cl$_2$ wash | 1.5 | 2 |
| 4. | DMF wash | 1.5 | 2 |
| 5. | i-PrOH wash | 1.5 | 2 |
| 6. | DMF/CH$_2$Cl$_2$/(1/1) | 1.5 | 2 |
| 7. | i-PrOH | 1.5 | 2 |
| 8. | CH$_2$Cl$_{2\text{wash}}$ | 1.5 | 3 |

The resin was then washed by repeating steps 3 to 8, and capped using the following protocol:

| STEP | EVENT | TIME (MINS) | REPETITIONS |
|------|-------|-------------|-------------|
| 9. | DMF wash | 15 | 1 |
| 10. | PhCOCl(0.18 M)/pyridine(0.36 M) in DMF/CH$_2$Cl$_2$ | 30–180 | 1 |

-continued

| STEP | EVENT | TIME (MINS) | REPETITIONS |
|---|---|---|---|
| 11. | CH$_2$Cl$_{2\text{wash}}$ | 1.5 | 2 |
| 12. | DMF wash | 1.5 | 2 |
| 13. | iPrOH | 1.5 | 2 |
| 14. | DMF/CH$_2$Cl$_{2(1/1)}$ wash | 1.5 | 1 |
| 15. | CH$_2$Cl$_2$ wash | 1.5 | 1 |

The remaining amino acids were attached to the resin in successive coupling cycles in reverse sequence using the following protected amino acids:

aa11 N$^\alpha$-Fmoc-N$^\epsilon$-t-butyloxycarbonyl-L-lysine
aa10 N$^\alpha$-Fmoc-L-aspartic acid-β-t-butyl ester
aa9 N$^\alpha$-Fmoc-N$^{im}$-trityl-L-histidine
aa8 N$^\alpha$-Fmoc-L-leucine
aa7 N$^\alpha$-Fmoc-L-leucine
aa6 N$^\alpha$-Fmoc-N$^g$-trityl-L-glutamine
aa5 N$^\alpha$-Fmoc-N$^{im}$-trityl-L-histidine
aa4 N$^\alpha$-Fmoc-L-glutamic acid-γ-t-butyl ester
aa3 N$^\alpha$-Fmoc-O-t-butyl-L-serine
aa2 N$^\alpha$-Fmoc-L-valine
aa1 N$^\alpha$-t-Butyloxycarbonyl-L-alanine The couplings were carried out at room temperature in NMP using 1.5 to 2.2 equivalents of amino acid (0.1–0.25M), HOBt, and DIC. After 1.5–3 hours, DMSO was added and the coupling continued for 1.5–3 hours. Each coupling involved the following steps:

| STEP | EVENT | TIME (MINS) | REPETITIONS |
|---|---|---|---|
| 1. | DMF wash | 2.5–30 | 1 |
| 2. | 20% piperidine in NMP | 3 | 1 |
| 3. | 20% piperidine in NMP | 14 | 1 |
| 4. | DMF wash | 1.5 | 2 |
| 5. | CH$_2$Cl$_2$ wash | 1.5 | 2 |
| 6. | iPrOH wash | 1.5–2.5 | 2–5 |
| 7. | DMF/CH$_2$Cl$_2$ (1/1) wash | 1.5 | 2–3 |
| 8. | Coupling | 240 | 1 |
| 9. | CH$_2$Cl$_2$ wash | 1.5 | 2 |
| 10. | DMF wash | 1.5 | 2 |
| 11. | i-PrOH wash | 1.5 | 2 |
| 12. | DMF/CH$_2$Cl$_{2\text{wash}}$ | 1.5 | 2 |
| 13. | iPrOH | 1.5 | 1 |
| 14. | CH$_2$Cl$_{2\text{wash}}$ | 1.5 | 3 |

Coupling completeness was confirmed by the Kaiser test; if the test was positive, steps 8 to 14 were repeated, optionally using PyBOP as the coupling agent.

To cleave the protected peptide from the resin, a suspension of the resin was stirred in 1% TFA in CH$_2$Cl$_2$ (4 mL/gm resin) at 0° C. or room temperature for up to 15 minutes. The solution was filtered and extracted with 5% NaHCO$_3$. TFA treatment of the resin was repeated three times. The organics were combined and washed with water, 5% NaHSO$_4$, and water again. The organic phase was dried over sodium sulfate and evaporated. The residue was purified by HPLC as follows:

Column: Zorbax Pro-10/150 C8, 6"×40 cm
Column temperature: ambient Flow rate: 2.2–3.0 mL/min. cm$^2$.
Detector wavelength: 250 nm
Mobile phase: 0.1% HOAc, pH 6–6.2 with triethylamine, CH$_3$CN The protected peptide was loaded on the column in 65–70% CH$_3$CN. A gradient was run increasing the proportion of CH$_3$CN to 85%. Fractions were combined, concentrated, and the product isolated by CH$_2$Cl$_2$ extraction. The organic phase was washed with a dilute solution of sodium bicarbonate or water, dried over sodium sulfate, filtered, and evaporated.

EXAMPLE 2

Preparation of the Middle Fragment

The middle fragment, consisting of amino acids 13 to 23, KSIQDLRRREL, was prepared on a 230 mmole scale on an acid sensitive resin, 4-hydroxymethyl-3-methoxyphenoxybutyric acid 4-methylbenzhydrylamine (HMPB-MBHA). This resin was prepared from MBHA resin as described above for Example 1. The first amino acid (aa24) was incorporated as shown using Fmoc-L-leucine. The remaining amino acids were attached to the resin in successive coupling cycles using the procedure of Example 1:

aa23 N$^\alpha$-Fmoc-L-glutamic acid-γ-t-butyl ester
aa22 N$^\alpha$-Fmoc-N$^g$-4-methoxy-2,3,6-trimethylbenzylsulfonyl-L-arginine
aa21 N$^\alpha$-Fmoc-N$^g$-4-methoxy-2,3,6-trimethylbenzylsulfonyl-L-arginine
aa20 N$^\alpha$-Fmoc-N$^g$-4-methoxy-2,3,6-trimethylbenzylsulfonyl-L-arginine
aa19 N$^\alpha$-Fmoc-L-leucine
aa18 N$^\alpha$-Fmoc-L-aspartic acid-β-t-butyl ester
aa17 N$^\alpha$-Fmoc-N$^g$-trityl-L-glutamine
aa16 N$^\alpha$-Fmoc-L-isoleucine
aa15 N$^\alpha$-Fmoc-O-t-butyl-L-serine
aa14 N$^\alpha$-Fmoc-N$^\epsilon$-t-butyloxycarbonyl-L-lysine The peptide was cleaved from the resin as the free acid, the organics extracted, dried and evaporated as taught for Example 1. The residue may be precipitated by dissolving in dichloromethane and adding to t-butyl methyl ether (t-BuOMe). After filtering, washing with t-BuOMe and vacuum drying, the product was purified by HPLC on a Zorbax column, described above, run isocratically with 75% CH$_3$CN; the detector wavelength was 267 nm.

EXAMPLE 3

Preparation of the C-Terminus Fragment

The C-terminus fragment, consisting of amino acids 24–34, LEKLLEKLHTA, was prepared on MBHA resin on a 130 mm scale using an Fmoc-2,4-dimethoxy-4'-(carboxymethyloxy)-benzhydrylamine linker as follows:

| STEP | EVENT | TIME (MINS) | REPETITIONS |
|---|---|---|---|
| 1. | CH$_2$Cl$_2$ wash | 60 | 1 |
| 2. | 10% DIPEA in CH$_2$Cl$_2$ | 5 | 2 |
| 3. | CH$_2$Cl$_2$ | 5 | 3 |
| 4. | DMF | 5 | 3 |
| 5. | Linker/HOBt/DIC (1.5 eq) in CH$_2$Cl$_2$/DMF (1/1) | 300–420 | 1 |
| 6. | CH$_2$Cl$_2$ | 1.5 | 2 |
| 7. | DMF | 1.5 | 2 |
| 8. | iPrOH | 2.5 | 2 |
| 9. | CH$_2$Cl$_2$/DMF | 1.5 | 2 |
| 10. | iPrOH | 2.5 | 2 |

-continued

| STEP | EVENT | TIME (MINS) | REPETITIONS |
|---|---|---|---|
| 11. | CH$_2$Cl$_2$ | 1.5 | 3 |
| 12. | DMF | 10 | 1 |
| 13. | Ac$_2$O, DIPEA in DMF/CH$_2$Cl$_2$ | 30–35 | 1 |
| 14. | CH$_2$Cl$_{2wash}$ | 1.5 | 2 |
| 15. | DMF wash | 1.5 | 2 |
| 16. | iPrOH wash | 1.5 | 2 |
| 17. | DMF/CH$_2$Cl$_{2wash}$ | 1.5 | 1 |
| 18 | CH$_2$Cl$_2$ wash | 1.5 | 3 |

The remaining amino acids were attached to the resin in successive coupling cycles in reverse sequence using the following protected amino acids:

aa34 N$^\alpha$-Fmoc-L-alanine
aa33 N$^\alpha$-Fmoc-O-t-butyl-L-threonine
aa32 N$^\alpha$-Fmoc-N$^{im}$-trityl-L-histidine
aa31 N$^\alpha$-Fmoc-L-leucine
aa30 N$^\alpha$-Fmoc-N$^\epsilon$-t-butyloxycarbonyl-L-lysine
aa29 N$^\alpha$-Fmoc-L-glutamic acid-γ-t-butyl ester
aa28 N$^\alpha$-Fmoc-L-leucine
aa27 N$^\alpha$-Fmoc-L-leucine
aa26 N$^\alpha$-Fmoc-N$^\epsilon$-t-butyloxycarbonyl-L-lysine
aa25 N$^\alpha$-Fmoc-L-glutamic acid-γ-t-butyl ester
aa24 N$^\alpha$-Fmoc-L-leucine The couplings were carried out for 1.5 to 3 hours at room temperature in NMP using 1.5 to 2.2 equivs. of amino acid, HOBt, and DIC, for amino acids 34 to 26. Three equivalents of amino acid, HOBt, and DIC were used for amino acids 24 and 25. After 1.5–3 hours, 20% DMSO was added and the coupling continued for 1.5–3 hours. Each coupling involved the following steps, including Fmoc cleavage and after coupling washes:

| STEP | EVENT | TIME (MINS) | REPETITIONS |
|---|---|---|---|
| 1. | DMF wash | 2.5–30 | 1 |
| 2. | 20% piperidine in NMP | 3 | 1 |
| 3. | 20% piperidine in NMP | 14 | 1 |
| 4. | DMF wash | 1.5 | 3 |
| 5. | CH$_2$Cl$_2$ wash | 1.5 | 2 |
| 6. | iprOH wash | 1.5–2.5 | 2–6 |
| 7. | DMF/CH$_2$Cl$_2$ (1/1) wash | 1.5 | 3 |
| 8. | Coupling | 240 | 2 |
| 9. | CH$_2$Cl$_2$ wash | 1.5 | 2 |
| 10. | DMF wash | 1.5 | 2 |
| 11. | iPrOH wash | 1.5–2.5 | 2 |
| 12. | DMF/CH$_2$Cl$_2$ wash | 1.5 | 2 |
| 13. | iPrOH | 2.5 | 1 |
| 14. | CH$_2$Cl$_2$ wash | 1.5 | 3 |
| 15. | DMF | 2.5–15 | 1 |
| 16. | Ac$_2$O/DIPEA/CH$_2$Cl$_2$/DMF | 30–35 | 1 |
| 17. | CH$_2$Cl$_2$ wash | 1.5 | 2 |
| 18. | DMF wash | 1.5 | 2 |
| 19. | iPrOH wash | 1.5 | 2 |
| 20. | DMF/CH$_2$Cl$_2$ wash | 1.5 | 1 |
| 21. | CH$_2$Cl$_2$ wash | 1.5 | 3 |

Coupling completeness was confirmed by the Kaiser test after each coupling step. If the test was positive ($\leq 1.5\%$ uncoupled), steps 8 to 14 were repeated; if the test was negative, the resin was acetylated.

EXAMPLE 4

Three Fragment Condensation

The three fragments were prepared as described above in Examples 1, 2 and 3. The remaining Nα-Fmoc group of the C-terminus fragment was removed using steps 1 to 7 of the last described Example 3 protocol.

The middle fragment B (172 g, 61.8 mmole), HOBt (59.2 mmole), HOAt (3.7 mmole), and DIC (61.9 mmole) were added to the C-terminal fragment resin (190 g, 41 mmole) in NMP (900 mL) and CH$_2$Cl$_2$. The mixture was stirred at room temperature for 22 hours. DIPEA (7 mL) was added and stirring continued for another day. The resin was washed as described in Example 1 (steps 9 to 13). A Kaiser test showed less than 2% uncoupled remaining. The resin was acetylated (Example 3, steps 14 to 20) and the Fmoc groups removed (Example 3, steps 1 to 7).

The N-terminus fragment A, as the Na salt, (153 g, 62.4 mmole), HOBt (59.2 mmole), HOAt (3.7 mmole), PyBOP (62.5 mmole) and DIPEA (125.15 mmole) were added to the resin in NMP (900 mL) and CH$_2$Cl$_2$. The mixture was stirred at room temperature for 24 hours, filtered and washed (Example 3, steps 9–13). The Kaiser test showed less than 1% uncoupled remaining. The resin was acetylated (Example 3, steps 14 to 20), removed from the reactor, and dried under vacuum.

A solution of phenol (60.3 g) in thioanisole (152.6 mL) and TFA (1 L) was added to the peptide-resin (64 g) under N$_2$. The mixture was cooled to −10° C. and TMSBr slowly added. The mixture was stirred for 0.5 hrs. at −10° C. in a closed system and for 1–2 hours at room temperature. The mixture was concentrated to half volume under vacuum at 50° C. and the resin was filtered and washed twice with TFA (250 mL) and glacial acetic acid (250 mL). The filtrates were precipitated by addition to a 3:1 mixture of t-butyl methyl ether:hexane (6.5 L). The crude peptide was filtered, washed with t-butyl methyl ether, toluene, and t-butyl methyl ether (2×250 mL each) and reprecipitated by dissolving in methanol (500 mL) and adding to t-butyl methyl ether (7 L). The crude was filtered, washed with t-butyl methyl ether, and dried under vacuum to yield 33 g of peptide.

In like manner, the following PTHrP analogs may be prepared, substituting an appropriate resin for the acid terminated peptides:

AVSEHQLLHDKGKSIQDLRRRELLEKLLEKLHTA-OH (SEQ ID NO:6)
AVSEHQLLHDKGKSIQDLRRRELLERLLERLHTA-OH (SEQ ID NO:15)
AVSEHQLLHDRGRSIQDLRRRELLERLLERLHTA-OH (SEQ ID NO:16)
AVSEHQLLHDRGRSIQDLRRRELLERLLKRLHTA-OH (SEQ ID NO:17)
AVSEHQLLHDKGKSIQDLRRRELLEKLLRKLHTA-OH (SEQ ID NO:5)
AVSEHQLLHDKGKSIQDLRRRELLEKLLEKLHTAGRR-OH (SEQ ID NO:10)
AVSEAQLLHDLGKSIQDLRRRELLEKLLEKLHAL-OH (SEQ ID NO:14)
AVSEHQLLHDKGKSIQDLRRRELLEKLLELLKEL-NH$_2$ (SEQ ID NO:11)
AVSEIQFXHNLGKHLSSXERVELLEKLLEKLHNY-NH$_2$ (X=Nle, SEQ ID NO:23)
AVSEIQFXHNLGKHLSSXRRRELLEKLLEKLHNY-NH$_2$ (X=Nle, SEQ ID NO:24)
AVSEHQLLHDKGKSIQDLRRRALAEALAEALHTA-NH$_2$ (SEQ ID NO:20)
AVSEHQLLHDKGKSIQDLARRELLEKLLEKLHTA-NH$_2$ (SEQ ID NO:12)
AVSEHQLLHDKGKSIQDLRRAELLEKLLEKLHTA-NH$_2$ (SEQ ID NO:13)
AVSEHQLLHDKGKSIQDLRRRSLLSSLLSSLHTA-NH$_2$ (SEQ ID NO:21)

AVSEHQLLHDKGKSIQDLRRRAFYDKVAEKLHTA-NH$_2$ (SEQ ID:NO:22)
AVSEIQFLHN LGKHLSSLRR RELLEKLLEK LHNY-NH$_2$ (SEQ ID NO:35)
AVSEHQLLHD KGKSIQDLKL KELLEKLLEK LHTA-NH$_2$ (SEQ ID NO:38)
AVSEHQLLHD KGKSIQDLRR RELLERLLER LHTA-NH$_2$ (SEQ ID NO:39)
AVSEHQLLHD KGKSIQDLRR RELLERLLER LHTAP-OH (SEQ ID NO:40)
AVSEHQLLHD KGKSIQDLRR RELLERLLER LHTAGRR-OH (SEQ ID NO:41)
AVSEHQLLHD KGKSIQDLRR RELLEKLLEK LHTY-NH$_2$ (SEQ ID NO:43)
AVSEHQLLHD KGYSIQDLRR RELLEKLLEK LHTA-NH$_2$ (SEQ ID NO:44)
AVSEHQLLHD KGCSIQDLRR RELLEKLLEK LHTA-NH$_2$ (SEQ ID NO:45)
AVSEHQLLHD KGXSIQDLRR RELLEKLLEK LHTA-NH$_2$ (SEQ ID NO:46)
   (X=Cys(CH$_2$CONH(CH$_2$)$_2$NH(biotinyl)))
AVSEHQLLHD KGXSIQDLRR RELLEKLLEK LHTA-NH$_2$ (SEQ ID NO:47)
   (X=Lys(7-dimethylamino-2-oxo-2H- 1-benxopyran-4-acetyl))
AVSEHQLLHD KGKSIQDLRR RELLEKLLEK LHTAG-OH (SEQ ID NO:48)
AVSX$_1$HQLLHX$_2$ KGKSIQX$_2$LRR RX$_1$LLX$_1$KLLX$_1$K LHA-OH (SEQ ID NO:49)
   (X$_1$=Glu(OCH$_3$); X$_2$=Asp(OCH$_3$))
AVSX$_1$HQLLHX$_2$ KGKSIQX$_2$LRR RX$_1$LLX$_1$KLLX$_1$K LHA-OCH$_3$(SEQ ID NO:50)
   (X$^{1=l\ =Glu(OCH}$$_3$); X$_2$=Asp(OCH$_3$))
AVSEHQLLHD KGKSIQDLRR RELLEKLLEK LHTAP-OH (SEQ ID NO:52)
AVSEHQLLHD KGKSIQDLRR RELLEKLLEK LHTP-OH (SEQ ID NO:53)
AVSEHQLLHD KGKSIQDLRR RELLEKLLEK LHTP-NH$_2$ (SEQ ID NO:54)
AVSEHQLLHD KGKSIQDLRR RELLEKLLEK LHP-NH$_2$ (SEQ ID NO:55)
AVSEHQLLHD KGKSIQDLRR RELLEKLLEK LP-NH$_2$ (SEQ ID NO:56)
AVSEHQLLHD KGKSIQDLRR RELLEKLLEK LHTRSAW-OH (SEQ ID NO:57)
AVSEHQLLHD RGRSIQDLRR RELLERLLER LHTAGRRTRSAW-OH (SEQ ID NO:58)
AVSEHQLLHD RGRSIQDLRR RELLERLLER LHTAGRRTRSAW-NH$_2$ (SEQ ID NO:59)
AVSEHQLLHD RGXSIQDLRR RELLERLLER LHTAGRRTRSAW-OH (SEQ ID NO:60)(X=Lys(dihydrocinnamoyl))
AVSEIQFXHN LGKHLSSXTR SAWLRKKLQD VHNY-NH$_2$ (SEQ ID NO:61)
   (X=norleucine)
AVSEHQLLHD KGKSIQDLRR RELLEKLLEK LHTMA-NH$_2$ (SEQ ID NO:62)
AVSEHQLLHD KGKSIQDLRR RFFLEKLLEK LHTA-NH$_2$ (SEQ ID NO:64)
AVSEHQLLHD KGKSIQDLRR RELLHKLLEK LHTA-NH$_2$ (SEQ ID NO:65)
AVSEHQLLHD KGKSIQDLRR RELLEHLLEK LHTA-NH$_2$ (SEQ ID NO:66)
AVSEHQLLHD KGKSIQDLRR RELLEKLIAK LHTA-NH$_2$ (SEQ ID NO:67)
AVSEHQLLHD KGKSIQDLRR RELLEKLLEE IHTA-NH$_2$ (SEQ ID NO:68)
AVSEHQLLHD KGKSIQDLRR RELLEKLLEK LHTRSAW-NH$_2$ (SEQ ID NO:72)
AVSEHQLLHD KGKSIQDLRR RELLEKLLEK LHTRSAX-OH (SEQ ID NO:73)
   (X=Nal(2)=3-(2-naphthyl)-L-alanine)
AVSEHQLLHD KGKSIQDLRR RELLEKLLEK LHTASAW-OH (SEQ ID NO:74)
AVSEHQLLHD KGKSIQDLRR RELLEKLLEK LHTAEIRA-OH (SEQ ID NO:75)
AVSEHQLLHD KGKSIQDLRR RELLEKLLEK LHTAEIR-OH (SEQ ID NO:76)
AVSEHQLLHD KGKSIQDLRR RELLEKLLEK LHTAEI-OH (SEQ ID NO:77)
AVSEHQLLHD KGKSIQDLRR RELLEKLLEK LHTAE-OH (SEQ ID:NO:78)
SEHQLLHD KGKSIQDLRR RELLEKLLEK LHTA-NH$_2$ (SEQ ID NO:80)
LLHD KGKSIQDLRR RELLEKLLEK LHTA-NH$_2$ (SEQ ID NO:81)
LHD KGKSIQDLRR RELLEKLLEK LHTA-NH$_2$ (SEQ ID NO:82)
SEHQLLHD RGRSIQDLRR RELLERLLER LHAGRRTRSAW-OH (SEQ ID NO:83)
LLHD RGRSIQDLRR RELLERLLER LHAGRRTRSAW-OH (SEQ ID NO:84)
[Met$^{34}$, Ala$^{35}$](SEQ ID NO:25),
AVSEHQLLHDKGKSIQDLRRRELLEKLLEKLHTMA-NH$_2$, (SEQ ID NO:25), may be prepared and purified following the procedures above. This polypeptide may be converted to the homoserine lactone as follows. The purified peptide is dissolved in 44% formic acid. This solution is combined with a premixed solution of cyanogen bromide (700 mgs) and phenol (1.6 mgs) in 44% formic acid at 0° C. The solution is stirred at 0° C. for 2 hr and at room temperature for 2 hrs. The formation of the product may be monitored by HPLC (Vydac® C-18, 300 A, 4.6×250 mm, flow of 1.2 mL/min, gradient 25–45% acetonitrile in 0.1% TFA over 10 min). The sample is concentrated and purified by preparative RP-HPLC (Vydac® C-18, gradient 25–45% acetonitrile in 0.1% TFA) to yield (SEQ ID NO:9).

AVSEHQLLHDKGKSIQDLRRRELLEKLLEKLHTX (X=hSerlac, SEQ ID NO:9)

Similarly, (SEQ ID NO:79) may be prepared in accordance with this procedure.

AVSEIQFX$_1$HN KGKHLSSX$_1$ER VEWLRKKLQD VHNX$_2$ (SEQ ID NO:79)
   (X$^1$=L-norleucine; X$_2$=homoserine lactone)

To prepare the homoserine amide, the crude hSerlactone analog, Compound 4, is concentrated and treated with 25 mL saturated NH$_3$ in methanol. The solution is stirred at 0° C. for 2 hr and at room temperature for 16 hr. The reaction may be monitored by HPLC (Vydac® C-18, 300 A, 4.6×250 mm, flow of 1.2 mL/min, gradient 20–45% acetonitrile in 0.1% TFA). The solution is concentrated and purified by preparative RP-HPLC (Vydac® C-18, gradient of 25–45% acetonitrile in 0.1% TFA). The homoserine amide peptide fractions are pooled and lyophilized to give (SEQ ID NO:8).

AVSEHQLLHDKGKSIQDLRRRELLEKLLEKLHTX-NH$_2$ (X=hSer, SEQ ID NO:8)

Similarly, Compounds 22, 23 and 28 may be prepared following this procedure, using methionine as C-terminus.

AVSEIQFLHN LGKHLSSLRR RELLEKLLEK LHNX-NH₂ (SEQ ID NO:36)
(X=homoserine)
AVSEIQFLHN KGKHLSSLRR RELLEKLLEK LHNX-NH₂ (SEQ ID NO:37)
(X=homoserine)
AVSEHQLLHD KGKSIQDLRR RELLERLLER LHTAGRRX-NH₂ (SEQ ID NO:42)
(X=homoserine)

The homoserine alkylamides are similarly prepared from the homoserine lactone by dissolving it in DMF containing an excess of the corresponding alkylamine. After stirring at room temperature for several days (the reaction may be monitored by analytical HPLC) the mixture is evaporated to dryness and the peptide purified by preparative HPLC. Representative homoserine alkylamides are Compounds 55 and 56.

AVSEHQLLHD KGKSIQDLRR RELLEKLLEK LHTX-NHCH₂CH₃ (SEQ ID NO:69)
(X=homoserine)
AVSEHQLLHD KGKSIQDLRR RELLEKLLEK LHTX-NHCH₂CH₂C₆H₅ (SEQ ID NO:70)
(X=homoserine)

An aqueous solution of the homoserine lactone analog above may be treated with porcine liver esterase (Sigma Chemical Company, St. Louis, Mo.). The hydrolysis of the lactone to the C-terminal homoserine may be monitored by analytical HPLC. When the hydrolysis is judged to be complete the material may be purified by preparative HPLC as above.

AVSEHQLLHD KGKSIQDLRR RELLEKLLEK LHTX-OH (SEQ ID NO:51)
(X=homoserine)

While this invention has been exemplified by the disclosure of the synthesis of a 34 amino acid polypeptide from three fragments, it is equally applicable to the synthesis of other PTH and PTHrP analogs of different lengths from different fragments. The number and length of the fragments is within the purview of the skilled artisan. Generally, glutamic acid, glycine, leucine and proline are desirable fragment C-termini. In the preceding Examples, leucine-leucine coupling between fragments 2 and 3 provided unexpectedly high yields. Similarly, leucine-leucine coupling could be exploited by the preparation of the polypeptide of SEQ ID NO:7 from fragments 1–7, 8–23, 24–27, and 28–34. In another embodiment when amino acids 24–27 (LEKL) are the same as 28–31, the four amino acid fragment may be prepared, by either solution or solid phase techniques, and condensed with itself to provide fragment 24–31. Alternatively, the four amino acid fragment 23–26 (LLEK) may be prepared and self-condensed to provide the 23–30 fragment. The ease of purification is enhanced with the use of smaller fragments, which readily crystallize; however, an increase in the number of fragments requires more fragment condensation steps.

The preceding written description provides a full, clear, concise and exact disclosure of the invention so as to enable one skilled in the art of peptide synthesis to make and use the same. This disclosure should not be construed so as to impart any direct or implied limitation upon the scope of the invention which is particularly pointed out and distinctly claimed below.

I claim:

1. A process for the synthesis of a synthetic polypeptide analog of parathyroid hormone (PTH) or parathyroid hormone related peptide (PTHrP), or salt thereof, in which amino acid residues (22–31) form an amphipathic α-helix, said residues (22–31) selected from the group consisting of (SEQ ID NOS: 85, 86, 26, 27, 28, 29, and 30), which process comprises:
   a) independently synthesizing precursor peptide fragments of the desired polypeptide on a solid resin support;
   b) cleaving all but the intended ultimate C-terminal precursor peptide fragment of the desired polypeptide from their respective resin supports;
   c) sequentially condensing said cleaved precursor peptide fragments with the resin bound C-terminal peptide fragment to form the desired polypeptide product;
   d) removing side chain protecting groups; and
   e) cleaving the polypeptide product from the resin support, wherein at least two of the fragments are coupled via leucine-leucine bonding.

2. A process of claim 1 in which the polypeptide product is prepared from three precursor peptide fragments: an N-terminus, a middle, and a C-terminus fragment.

3. A process of claim 2 in which the N-terminus fragment has a C-terminal glycine, the middle fragment has a C-terminal leucine, and the C-terminus fragment has an N-terminal leucine.

4. A process of claim 3 in which the final polypeptide product comprises a PTH or PTHrP analog of the formula:

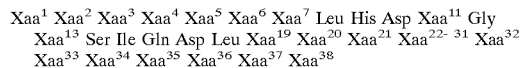

Term, wherein:
   $Xaa^1$ is absent or is Ala;
   $Xaa^2$ is absent or is Val;
   $Xaa^3$ is absent or is Ser;
   $Xaa^4$ is absent or is Glu or Glu(OCH$_3$);
   $Xaa^5$ is absent or is His or Ala;
   $Xaa^6$ is absent or is Gln;
   $Xaa^7$ is absent or is Leu;
   $Xaa^{11}$ is Lys, Arg, or Leu;
   $Xaa^{13}$ is Lys, Arg, Tyr, Cys, Leu, Cys(CH$_2$CONH(CH$_2$)$_2$NH(biotinyl)), Lys(7-dimethylamino-2-oxo-2H-1-benxopyran-4-acetyl), or Lys(dihydrocinnamoyl);
   $Xaa^{20}$ is Arg or Leu;
   $Xaa^{19}$ and $Xaa^{21}$ are independently Lys, Ala, or Arg;
   $Xaa^{22-31}$ is selected from (SEQ ID NOS:85, 86, 26, 27, 28, 29, or 30); $Xaa^{32}$ is His, Pro, or Lys;
   $Xaa^{33}$ is absent, or is Pro, Thr, Glu, or Ala;
   $Xaa^{34}$ is absent, or is Pro, Arg, Met, Ala, hSer, hSer lactone, Tyr, or Leu;
   $Xaa^{35}$ is absent or is Pro, Glu, Ser, Ala, or Gly;
   $Xaa^{36}$ is absent or is Ala, Arg, or Ile;
   $Xaa^{37}$ is absent or is Arg, Trp, or 3-(-2-naphthyl)-L-alanine;
   $Xaa^{38}$ is absent or is Ala or hSer or $Xaa^{38-42}$ is Thr Arg Ser Ala Trp; and
Term is
   OR or NR$_2$ where each R is independently H, (C$_1$–C$_4$) alkyl or phenyl(C$_1$–C$_4$)alkyl; and the pharmaceutically acceptable salts thereof.

5. A process of claim 4 in which the polypeptide product is prepared from three precursor peptide fragments: an N-terminus, a middle, and a C-terminus fragment.

6. A process of claim 1 in which the polypeptide analog of PTH or PTHrP comprises the formula:

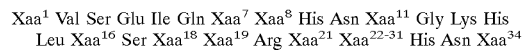

Term, wherein:
   $Xaa^1$ is Ser or Ala;
   $Xaa^7$ is Leu or Phe;
   $Xaa^8$ is Leu, Met, or Nle;
   $Xaa^{11}$ is Leu or Lys;
   $Xaa^{16}$ is Asn or Ser;
   $Xaa^{18}$ is Leu, Met, or Nle;
   $Xaa^{19}$ is Glu, Thr, or Arg;
   $Xaa^{21}$ is Val, Ser, or Arg;
   $Xaa^{22-31}$ is selected from (SEQ ID NOS: 26, 27, 28, 29, or 30); $Xaa^{34}$ is Phe, hSer, or Tyr;
Term is
   OR or NR$_2$, where R is H or a (C$_1$–C$_4$)alkyl; and the pharmaceutically acceptable salts thereof.

7. A process of claim 6 in which the polypeptide product is prepared from three precursor peptide fragments: an N-terminus, a middle, and a C-terminus fragment.

8. A process of claim 1 in which the PTH or PTHrP analog is selected from the group consisting of:
AVSEHQLLHDKGKSIQDLRRRELLEKLLEKLHTA-NH$_2$ (SEQ ID NO:7)
AVSEHQLLHDKGKSIQDLRRRELLEKLLEKLHTA-OH (SEQ ID NO:6)
AVSEHQLLHDKGKSIQDLRRRELLERLLERLHTA-OH (SEQ ID NO:15)
AVSEHQLLHDRGRSIQDLRRRELLERLLERLHTA-OH (SEQ ID NO:16)
AVSEHQLLHDRGRSIQDLRRRELLERLLKRLHTA-OH (SEQ ID NO:17)

AVSEHQLLHDKGKSIQDLRRRELLEKLLRKLHTA-OH (SEQ ID NO:5)
AVSEHQLLHDKGKSIQDLRRRELLEKLLEKLHTAGRR-OH (SEQ ID NO:10)
AVSEAQLLHDLGKSIQDLRRRELLEKLLEKLHAL-OH (SEQ ID NO:14)
AVSEHQLLHDKGKSIQDLRRRELLEKLLELLKEL-NH$_2$ (SEQ ID NO:11)
AVSEIQFXHNLGKHLSSXERVELLEKLLEKLHNY-NH$_2$ (X=Nle, SEQ ID NO:23)
AVSEIQFXHNLGKHLSSXRRRELLEKLLEKLHNY-NH$_2$ (X=Nle, SEQ ID NO:24)
AVSEHQLLHDKGKSIQDLRRRALAEALAEALHTA-NH$_2$ (SEQ ID NO:20)
AVSEHQLLHDKGKSIQDLARRELLEKLLEKLHTA-NH$_2$ (SEQ ID NO:12)
AVSEHQLLHDKGKSIQDLRRAELLEKLLEKLHTA-NH$_2$ (SEQ ID NO:13)
AVSEHQLLHDKGKSIQDLRRRSLLSSLLSSLHTA-NH$_2$ (SEQ ID NO:21)
AVSEHQLLHDKGKSIQDLRRRAFYDKVAEKLHTA-NH$_2$ (SEQ ID NO:22)
AVSEIQFLHN LGKHLSSLRR RELLEKLLEK LHNY-NH$_2$ (SEQ ID NO:35)
AVSEHQLLHD KGKSIQDLKL KELLEKLLEK LHTA-NH$_2$ (SEQ ID NO:38)
AVSEHQLLHD KGKSIQDLRR RELLERLLER LHTA-NH$_2$ (SEQ ID NO:39)
AVSEHQLLHD KGKSIQDLRR RELLERLLER LHTAP-OH (SEQ ID NO:40)
AVSEHQLLHD KGKSIQDLRR RELLERLLER LHTAGRR-OH (SEQ ID NO:41)
AVSEHQLLHD KGKSIQDLRR RELLEKLLEK LHTY-NH$_2$ (SEQ ID NO:43)
AVSEHQLLHD KGYSIQDLRR RELLEKLLEK LHTA-NH$_2$ (SEQ ID NO:44)
AVSEHQLLHD KGCSIQDLRR RELLEKLLEK LHTA-NH$_2$ (SEQ ID NO:45)
AVSEHQLLHD KGXSIQDLRR RELLEKLLEK LHTA-NH$_2$ (SEQ ID NO:46)
(X=Cys(CH$_2$CONH(CH$_2$)$_2$NH(biotinyl))
AVSEHQLLHD KGXSIQDLRR RELLEKLLEK LHTA-NH$_2$ (SEQ ID NO:47)
(X=Lys(7-dimethylamino-2-oxo-2H-1-benxopyran-4-acetyl))
AVSEHQLLHD KGKSIQDLRR RELLEKLLEK LHTAG-OH (SEQ ID NO:48)
AVSX$_1$HQLLHX$_2$ KGKSIQX$_2$LRR RX$_1$LLX$_1$KLLX$_1$K LHA-OH (SEQ ID NO:49)
(X$_1$=Glu(OCH$_3$); X$_2$=Asp(OCH$_3$))
AVSX$_1$HQLLHX$_2$ KGKSIQX$_2$LRR RX$_1$LLX$_1$KLLX$_1$K LHA-OCH$_3$ (SEQ ID NO:50)
(X$_1$=Glu(OCH$_3$); X$_2$=Asp(OCH$_3$))
AVSEHQLLHD KGKSIQDLRR RELLEKLLEK LHTAP-OH (SEQ ID NO:52)
AVSEHQLLHD KGKSIQDLRR RELLEKLLEK LHTP-OH (SEQ ID NO:53)
AVSEHQLLHD KGKSIQDLRR RELLEKLLEK LHTP-NH$_2$ (SEQ ID NO:54)
AVSEHQLLHD KGKSIQDLRR RELLEKLLEK LHP-NH$_2$ (SEQ ID NO:55)
AVSEHQLLHD KGKSIQDLRR RELLEKLLEK LP-NH$_2$ (SEQ ID NO:56)
AVSEHQLLHD KGKSIQDLRR RELLEKLLEK LHTRSAW-OH (SEQ ID NO:57)
AVSEHQLLHD RGRSIQDLRR RELLERLLER LHTAGRRTRSAW-OH (SEQ ID NO:58)
AVSEHQLLHD RGRSIQDLRR RELLERLLER LHTAGRRTRSAW-NH$_2$ (SEQ ID NO:59)
AVSEHQLLHD RGXSIQDLRR RELLERLLER LHTAGRRTRSAW-OH (SEQ ID NO:60)
(X=Lys(dihydrocinnamoyl))
AVSEIQFXHN LGKHLSSXTR SAWLRKKLQD VHNY-NH$_2$ (SEQ ID NO:61)
(X=norleucine)
AVSEHQLLHD KGKSIQDLRR RELLEKLLEK LHTMA-NH$_2$ (SEQ ID NO:62)
AVSEHQLLHD KGKSIQDLRR RFFLEKLLEK LHTA-NH$_2$ (SEQ ID NO:64)
AVSEHQLLHD KGKSIQDLRR RELLHKLLEK LHTA-NH$_2$ (SEQ ID NO:65)
AVSEHQLLHD KGKSIQDLRR RELLEHLLEK LHTA-NH$_2$ (SEQ ID NO:66)
AVSEHQLLHD KGKSIQDLRR RELLEKLIAK LHTA-NH$_2$ (SEQ ID NO:67)
AVSEHQLLHD KGKSIQDLRR RELLEKLLEE IHTA-NH$_2$ (SEQ ID NO:68)
AVSEHQLLHD KGKSIQDLRR RELLEKLLEK LHTRSAW-NH$_2$ (SEQ ID NO:72)
AVSEHQLLHD KGKSIQDLRR RELLEKLLEK LHTRSAX-OH (SEQ ID NO:73)
(X=Nal(2)=3-(2-naphthyl)-L-alanine)
AVSEHQLLHD KGKSIQDLRR RELLEKLLEK LHTASAW-OH (SEQ ID NO:74)
AVSEHQLLHD KGKSIQDLRR RELLEKLLEK LHTAEIRA-OH (SEQ ID NO:75)
AVSEHQLLHD KGKSIQDLRR RELLEKLLEK LHTAEIR-OH (SEQ ID NO:76)
AVSEHQLLHD KGKSIQDLRR RELLEKLLEK LHTAEI-OH (SEQ ID NO:77)
AVSEHQLLHD KGKSIQDLRR RELLEKLLEK LHTAE-OH (SEQ ID NO:78)
SEHQLLHD KGKSIQDLRR RELLEKLLEK LHTA-NH$_2$ (SEQ ID NO:80)
LLHD KGKSIQDLRR RELLEKLLEK LHTA-NH$_2$ (SEQ ID NO:81)
LHD KGKSIQDLRR RELLEKLLEK LHTA-NH$_2$ (SEQ ID NO:82)
SEHQLLHD RGRSIQDLRR RELLERLLER LHAGRRTRSAW-OH (SEQ ID NO:83)
LLHD RGRSIQDLRR RELLERLLER LHAGRRTRSAW-OH (SEQ ID NO:84)
AVSEHQLLHDKGKSIQDLRRRELLEKLLEKLHTX (X=hSerlac, SEQ ID NO:9)
AVSEIQFX$_1$HN KGKHLSSX$_1$ER VEWLRKKLQD VHNX$_2$ (SEQ ID NO:79)
(X$_1$=L-norleucine; X$_2$=homoserine lactone)
AVSEHQLLHDKGKSIQDLRRRELLEKLLEKLHTX-NH$_2$ (X=hSer, SEQ ID NO:8)
AVSEIQFLHN LGKHLSSLRR RELLEKLLEK LHNX-NH$_2$ (SEQ ID NO:36)
(X=homoserine)
AVSEIQFLHN KGKHLSSLRR RELLEKLLEK LHNX-NH$_2$ (SEQ ID NO:37)
(X=homoserine)
AVSEHQLLHD KGKSIQDLRR RELLERLLER LHTAGRRX-NH$_2$ (SEQ ID NO:42)
(X=homoserine)
AVSEHQLLHD KGKSIQDLRR RELLEKLLEK LHTX-NHCH$_2$CH$_3$ (SEQ ID NO:69)
(X=homoserine)
AVSEHQLLHD KGKSIQDLRR RELLEKLLEK LHTX-NHCH$_2$CH$_2$C$_6$CH$_5$ (SEQ ID NO:70)

(X=homoserine), and
AVSEHQLLHD KGKSIQDLRR RELLEKLLEK LHTX-OH (SEQ ID NO:51)
(X=homoserine).

9. A process of claim 8 in which the polypeptide product is prepared from three precursor peptide fragments: an N-terminus, a middle, and a C-terminus fragment.

10. A process for the synthesis of the polypeptide of SEQ ID NO:7, AVSEHQLLHDKGKSIQDLRRRELLEKLLEKLHTA-NH$_2$, which process comprises:

a) independently synthesizing precursor peptide fragments of SEQ ID NO:7 on a solid resin support;

b) cleaving all but the intended ultimate C-terminal precursor peptide fragment of SEQ ID NO:7 from their respective resin supports;

c) sequentially condensing said cleaved precursor peptide fragments with the resin bound C-terminal peptide fragment to form the polypeptide of SEQ ID NO:7;

d) removing side chain protecting groups; and e) cleaving the polypeptide of SEQ ID NO:7 from the resin support, wherein at least two of the fragments are coupled via leucine-leucine bonding.

11. A process of claim 10 in which the polypeptide product is prepared from three precursor peptide fragments: an N-terminus, a middle, and a C-terminus fragment.

12. A process of claim 11 wherein said first fragment comprises AVSEHQLLHDKG (SEQ ID No. 87) said second fragment comprises KSIQDLRRREL (SEQ ID No. 88), and said third fragment comprises LEKLLEKLHTA (SEQ ID No. 89).

13. A process of claim 12 wherein said third fragment is formed by the condensation of LEKL, LEKL, and HTA.

14. The synthetic polypeptide of the sequence AVSEHQLLHDKG (SEQ ID No. 87).

15. The synthetic polypeptide of the sequence KSIQDLRRREL (SEQ ID No. 88).

16. The synthetic polypeptide of the sequence LEKLLEKLHTA (SEQ ID No. 89).

17. The synthetic polypeptide of the formula KSIQDLRRRE (SEQ ID No. 90).

18. The synthetic polypeptide of the formula LLEKLLEKLHTA (SEQ ID No. 91).

19. The process of claim 1 wherein the resin bound C-terminal peptide fragment comprises between 6 and 12 amino acids.

20. The process of claim 10 wherein the resin bound C-terminal peptide fragment comprises between 6 and 12 amino acids.

* * * * *

SEQUENCE LISTING

```
<160> NUMBER OF SEQ ID NOS: 91

<210> SEQ ID NO 1
<211> LENGTH: 34
<212> TYPE: PRT
<213> ORGANISM: Homo sapiens

<400> SEQUENCE: 1

Ser Val Ser Glu Ile Gln Leu Met His Asn Leu Gly Lys His Leu Asn
 1               5                  10                  15

Ser Met Glu Arg Val Glu Trp Leu Arg Lys Lys Leu Gln Asp Val His
            20                  25                  30

Asn Phe

<210> SEQ ID NO 2
<211> LENGTH: 34
<212> TYPE: PRT
<213> ORGANISM: bovine

<400> SEQUENCE: 2

Ala Val Ser Glu Ile Gln Phe Met His Asn Leu Gly Lys His Leu Ser
 1               5                  10                  15

Ser Met Glu Arg Val Glu Trp Leu Arg Lys Lys Leu Gln Asp Val His
            20                  25                  30
```

Asn Phe

<210> SEQ ID NO 3
<211> LENGTH: 34
<212> TYPE: PRT
<213> ORGANISM: Porcine

<400> SEQUENCE: 3

Ser Val Ser Glu Ile Gln Leu Met His Asn Leu Gly Lys His Leu Ser
 1               5                  10                  15

Ser Leu Glu Arg Val Glu Trp Leu Arg Lys Lys Leu Gln Asp Val His
                20                  25                  30

Asn Phe

<210> SEQ ID NO 4
<211> LENGTH: 34
<212> TYPE: PRT
<213> ORGANISM: Homo sapiens

<400> SEQUENCE: 4

Ala Val Ser Glu His Gln Leu Leu His Asp Lys Gly Lys Ser Ile Gln
 1               5                  10                  15

Asp Leu Arg Arg Arg Phe Phe Leu His His Leu Ile Ala Glu Ile His
                20                  25                  30

Thr Ala

<210> SEQ ID NO 5
<211> LENGTH: 34
<212> TYPE: PRT
<213> ORGANISM: Homo sapiens

<400> SEQUENCE: 5

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Arg Lys Leu His
                20                  25                  30

Thr Ala

<210> SEQ ID NO 6
<211> LENGTH: 34
<212> TYPE: PRT
<213> ORGANISM: Homo sapiens

<400> SEQUENCE: 6

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
                20                  25                  30

Thr Ala

<210> SEQ ID NO 7
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 7

Ala Val Ser Glu His Gln Leu Leu His Asp Lys Gly Lys Ser Ile Gln

```
            1               5              10              15

Asp Leu Arg Arg Arg Glu Leu Leu Glu Lys Leu Leu Glu Lys Leu His
                20                  25                  30

Thr Ala

<210> SEQ ID NO 8
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION
<220> FEATURE:
<221> NAME/KEY: MOD_RES
<222> LOCATION: (34)
<223> OTHER INFORMATION: homoserine

<400> SEQUENCE: 8

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
                20                  25                  30

Thr Xaa

<210> SEQ ID NO 9
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: homoserinelactone

<400> SEQUENCE: 9

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
                20                  25                  30

Thr Xaa

<210> SEQ ID NO 10
<211> LENGTH: 37
<212> TYPE: PRT
<213> ORGANISM: Homo sapiens

<400> SEQUENCE: 10

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
                20                  25                  30

Thr Ala Gly Arg Arg
             35

<210> SEQ ID NO 11
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 11
```

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu Lys
            20                  25                  30

Glu Leu

<210> SEQ ID NO 12
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 12

Ala Val Ser Glu His Gln Leu Leu His Asp Lys Gly Lys Ser Ile Gln
 1               5                  10                  15

Asp Leu Ala Arg Arg Glu Leu Leu Glu Lys Leu Leu Glu Lys Leu His
            20                  25                  30

Thr Ala

<210> SEQ ID NO 13
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 13

Ala Val Ser Glu His Gln Leu Leu His Asp Lys Gly Lys Ser Ile Gln
 1               5                  10                  15

Asp Leu Arg Arg Ala Glu Leu Leu Glu Lys Leu Leu Glu Lys Leu His
            20                  25                  30

Thr Ala

<210> SEQ ID NO 14
<211> LENGTH: 34
<212> TYPE: PRT
<213> ORGANISM: Homo sapiens

<400> SEQUENCE: 14

Ala Val Ser Glu Ala Gln Leu Leu His Asp Leu Gly Lys Ser Ile Gln
 1               5                  10                  15

Asp Leu Arg Arg Arg Glu Leu Leu Glu Lys Leu Leu Glu Lys Leu His
            20                  25                  30

Ala Leu

<210> SEQ ID NO 15
<211> LENGTH: 34
<212> TYPE: PRT
<213> ORGANISM: Homo sapiens

<400> SEQUENCE: 15

Ala Val Ser Glu His Gln Leu Leu His Asp Lys Gly Lys Ser Ile Gln
 1               5                  10                  15

Asp Leu Arg Arg Arg Glu Leu Leu Glu Arg Leu Leu Glu Arg Leu His
            20                  25                  30

<210> SEQ ID NO 16
<211> LENGTH: 34
<212> TYPE: PRT
<213> ORGANISM: Homo sapiens

<400> SEQUENCE: 16

Ala Val Ser Glu His Gln Leu Leu His Asp Arg Gly Arg Ser Ile Gln
 1               5                  10                  15

Asp Leu Arg Arg Arg Glu Leu Leu Glu Arg Leu Leu Glu Arg Leu His
            20                  25                  30

Thr Ala

<210> SEQ ID NO 17
<211> LENGTH: 34
<212> TYPE: PRT
<213> ORGANISM: Homo sapiens

<400> SEQUENCE: 17

Ala Val Ser Glu His Gln Leu Leu His Asp Arg Gly Arg Ser Ile Gln
 1               5                  10                  15

Asp Leu Arg Arg Arg Glu Leu Leu Glu Arg Leu Leu Lys Arg Leu His
            20                  25                  30

Thr Ala

<210> SEQ ID NO 18
<211> LENGTH:
<212> TYPE:
<213> ORGANISM:

<400> SEQUENCE: 18

This Sequence is intentionally skipped

<210> SEQ ID NO 19
<211> LENGTH:
<212> TYPE:
<213> ORGANISM:

<400> SEQUENCE: 19

This Sequence is intentionally skipped

<210> SEQ ID NO 20
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 20

Ala Val Ser Glu His Gln Leu Leu His Asp Lys Gly Lys Ser Ile Gln
 1               5                  10                  15

Asp Leu Arg Arg Arg Ala Leu Ala Glu Ala Leu Ala Glu Ala Leu His
            20                  25                  30

Thr Ala

<210> SEQ ID NO 21
<211> LENGTH: 34
<212> TYPE: PRT
<213> ORGANISM: Homo sapiens

```
<220> FEATURE:
<221> NAME/KEY: MOD_RES
<222> LOCATION: (34)
<223> OTHER INFORMATION: AMIDATION

<400> SEQUENCE: 21

Ala Val Ser Glu His Gln Leu Leu His Asp Lys Gly Lys Ser Ile Gln
 1               5                  10                  15
Asp Leu Arg Arg Arg Ser Leu Leu Ser Ser Leu Ser Leu His
            20                  25                  30
Thr Ala

<210> SEQ ID NO 22
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 22

Ala Val Ser Glu His Gln Leu Leu His Asp Lys Gly Lys Ser Ile Gln
 1               5                  10                  15
Asp Leu Arg Arg Arg Ala Phe Tyr Asp Lys Val Ala Glu Lys Leu His
            20                  25                  30
Thr Ala

<210> SEQ ID NO 23
<211> LENGTH: 34
<212> TYPE: PRT
<213> ORGANISM: Homo sapiens
<220> FEATURE:
<221> NAME/KEY: MOD_RES
<222> LOCATION: (8)
<223> OTHER INFORMATION: Nle
<220> FEATURE:
<221> NAME/KEY: MOD_RES
<222> LOCATION: (18)
<223> OTHER INFORMATION: Nle
<220> FEATURE:
<221> NAME/KEY: MOD_RES
<222> LOCATION: (34)
<223> OTHER INFORMATION: AMIDATION

<400> SEQUENCE: 23

Ala Val Ser Glu Ile Gln Phe Xaa His Asn Leu Gly Lys His Leu Ser
 1               5                  10                  15
Ser Xaa Glu Arg Val Glu Leu Leu Glu Lys Leu Leu Glu Lys Leu His
            20                  25                  30
Asn Tyr

<210> SEQ ID NO 24
<211> LENGTH: 34
<212> TYPE: PRT
<213> ORGANISM: Homo sapiens
<220> FEATURE:
<221> NAME/KEY: MOD_RES
<222> LOCATION: (8)
<223> OTHER INFORMATION: Nle
<220> FEATURE:
<221> NAME/KEY: MOD_RES
<222> LOCATION: (18)
<223> OTHER INFORMATION: Nle
<220> FEATURE:
<221> NAME/KEY: MOD_RES
<222> LOCATION: (34)
```

```
<223> OTHER INFORMATION: AMIDATION

<400> SEQUENCE: 24

Ala Val Ser Glu Ile Gln Phe Xaa His Asn Leu Gly Lys His Leu Ser
 1               5                  10                  15

Ser Xaa Arg Arg Arg Glu Leu Leu Glu Lys Leu Leu Glu Lys Leu His
            20                  25                  30

Asn Tyr

<210> SEQ ID NO 25
<211> LENGTH: 35
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 25

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
            20                  25                  30

Thr Met Ala
         35

<210> SEQ ID NO 26
<211> LENGTH: 10
<212> TYPE: PRT
<213> ORGANISM: Homo sapiens
<220> FEATURE:
<221> NAME/KEY: MOD_RES
<222> LOCATION: (8)
<223> OTHER INFORMATION: Glu or Arg

<400> SEQUENCE: 26

Glu Leu Leu Glu Lys Leu Leu Xaa Lys Leu
 1               5                  10

<210> SEQ ID NO 27
<211> LENGTH: 10
<212> TYPE: PRT
<213> ORGANISM: Homo sapiens
<220> FEATURE:
<221> NAME/KEY: MOD_RES
<222> LOCATION: (8)
<223> OTHER INFORMATION: Glu or Lys

<400> SEQUENCE: 27

Glu Leu Leu Glu Arg Leu Leu Xaa Arg Leu
 1               5                  10

<210> SEQ ID NO 28
<211> LENGTH: 10
<212> TYPE: PRT
<213> ORGANISM: Homo sapiens

<400> SEQUENCE: 28

Ala Leu Ala Glu Ala Leu Ala Glu Ala Leu
 1               5                  10

<210> SEQ ID NO 29
<211> LENGTH: 10
<212> TYPE: PRT
<213> ORGANISM: Homo sapiens
```

```
<400> SEQUENCE: 29

Ser Leu Leu Ser Ser Leu Leu Ser Ser Leu
 1               5                  10

<210> SEQ ID NO 30
<211> LENGTH: 10
<212> TYPE: PRT
<213> ORGANISM: Homo sapiens

<400> SEQUENCE: 30

Ala Phe Tyr Asp Lys Val Ala Glu Lys Leu
 1               5                  10

<210> SEQ ID NO 31
<211> LENGTH:
<212> TYPE:
<213> ORGANISM:

<400> SEQUENCE: 31

This Sequence is intentionally skipped

<210> SEQ ID NO 32
<211> LENGTH:
<212> TYPE:
<213> ORGANISM:

<400> SEQUENCE: 32

This Sequence is intentionally skipped

<210> SEQ ID NO 33
<211> LENGTH:
<212> TYPE:
<213> ORGANISM:

<400> SEQUENCE: 33

This Sequence is intentionally skipped

<210> SEQ ID NO 34
<211> LENGTH:
<212> TYPE:
<213> ORGANISM:

<400> SEQUENCE: 34

This Sequence is intentionally skipped

<210> SEQ ID NO 35
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 35

Ala Val Ser Glu Ile Gln Phe Leu His Asn Leu Gly Lys His Leu Ser
 1               5                  10                  15

Ser Leu Arg Arg Arg Glu Leu Leu Glu Lys Leu Leu Glu Lys Leu His
            20                  25                  30

Asn Tyr

<210> SEQ ID NO 36
```

<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: homoserine
<220> FEATURE:
<221> NAME/KEY: MOD_RES
<222> LOCATION: (34)
<223> OTHER INFORMATION: AMIDATION

<400> SEQUENCE: 36

Ala Val Ser Glu Ile Gln Phe Leu His Asn Leu Gly Lys His Leu Ser
 1               5                  10                  15

Ser Leu Arg Arg Arg Glu Leu Leu Glu Lys Leu Leu Glu Lys Leu His
                20                  25                  30

Asn Xaa

<210> SEQ ID NO 37
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION
<220> FEATURE:
<221> NAME/KEY: MOD_RES
<222> LOCATION: (34)
<223> OTHER INFORMATION: homoserine

<400> SEQUENCE: 37

Ala Val Ser Glu Ile Gln Phe Leu His Asn Lys Gly Lys His Leu Ser
 1               5                  10                  15

Ser Leu Arg Arg Arg Glu Leu Leu Glu Lys Leu Leu Glu Lys Leu His
                20                  25                  30

Asn Xaa

<210> SEQ ID NO 38
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 38

Ala Val Ser Glu His Gln Leu Leu His Asp Lys Gly Lys Ser Ile Gln
 1               5                  10                  15

Asp Leu Lys Leu Lys Glu Leu Leu Glu Lys Leu Leu Glu Lys Leu His
                20                  25                  30

Thr Ala

<210> SEQ ID NO 39
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 39

Ala Val Ser Glu His Gln Leu Leu His Asp Lys Gly Lys Ser Ile Gln

```
                   1               5              10              15

Asp Leu Arg Arg Arg Glu Leu Leu Glu Arg Leu Leu Glu Arg Leu His
                20              25              30

Thr Ala

<210> SEQ ID NO 40
<211> LENGTH: 35
<212> TYPE: PRT
<213> ORGANISM: Homo sapiens

<400> SEQUENCE: 40

Ala Val Ser Glu His Gln Leu Leu His Asp Lys Gly Lys Ser Ile Gln
 1               5              10              15

Asp Leu Arg Arg Arg Glu Leu Leu Glu Arg Leu Leu Glu Arg Leu His
                20              25              30

Thr Ala Pro
            35

<210> SEQ ID NO 41
<211> LENGTH: 37
<212> TYPE: PRT
<213> ORGANISM: Homo sapiens

<400> SEQUENCE: 41

Ala Val Ser Glu His Gln Leu Leu His Asp Lys Gly Lys Ser Ile Gln
 1               5              10              15

Asp Leu Arg Arg Arg Glu Leu Leu Glu Arg Leu Leu Glu Arg Leu His
                20              25              30

Thr Ala Gly Arg Arg
            35

<210> SEQ ID NO 42
<211> LENGTH: 38
<212> TYPE: PRT
<213> ORGANISM: Homo sapiens
<220> FEATURE:
<221> NAME/KEY: MOD_RES
<222> LOCATION: (38)
<223> OTHER INFORMATION: AMIDATION
<220> FEATURE:
<221> NAME/KEY: MOD_RES
<222> LOCATION: (38)
<223> OTHER INFORMATION: homoserine

<400> SEQUENCE: 42

Ala Val Ser Glu His Gln Leu Leu His Asp Lys Gly Lys Ser Ile Gln
 1               5              10              15

Asp Leu Arg Arg Arg Glu Leu Leu Glu Arg Leu Leu Glu Arg Leu His
                20              25              30

Thr Ala Gly Arg Arg Xaa
            35

<210> SEQ ID NO 43
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 43

Ala Val Ser Glu His Gln Leu Leu His Asp Lys Gly Lys Ser Ile Gln
```

---continued

```
                1               5              10              15
Asp Leu Arg Arg Arg Glu Leu Leu Glu Lys Leu Leu Glu Lys Leu His
                    20              25              30

Thr Tyr

<210> SEQ ID NO 44
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 44

Ala Val Ser Glu His Gln Leu Leu His Asp Lys Gly Tyr Ser Ile Gln
 1               5              10              15

Asp Leu Arg Arg Arg Glu Leu Leu Glu Lys Leu Leu Glu Lys Leu His
                    20              25              30

Thr Ala

<210> SEQ ID NO 45
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 45

Ala Val Ser Glu His Gln Leu Leu His Asp Lys Gly Cys Ser Ile Gln
 1               5              10              15

Asp Leu Arg Arg Arg Glu Leu Leu Glu Lys Leu Leu Glu Lys Leu His
                    20              25              30

Thr Ala

<210> SEQ ID NO 46
<211> LENGTH: 34
<212> TYPE: PRT
<213> ORGANISM: Homo sapiens
<220> FEATURE:
<221> NAME/KEY: MOD_RES
<222> LOCATION: (13)
<223> OTHER INFORMATION: Cys(Ch2CONH(CH2)2NH(biotinyl))
<220> FEATURE:
<221> NAME/KEY: MOD_RES
<222> LOCATION: (34)
<223> OTHER INFORMATION: AMIDATION

<400> SEQUENCE: 46

Ala Val Ser Glu His Gln Leu Leu His Asp Lys Gly Xaa Ser Ile Gln
 1               5              10              15

Asp Leu Arg Arg Arg Glu Leu Leu Glu Lys Leu Leu Glu Lys Leu His
                    20              25              30

Thr Ala

<210> SEQ ID NO 47
<211> LENGTH: 34
<212> TYPE: PRT
<213> ORGANISM: Homo sapiens
<220> FEATURE:
<221> NAME/KEY: MOD_RES
<222> LOCATION: (13)
```

```
<223> OTHER INFORMATION: Lys(7-dimethylamino-2-oxo-2H-1-benxopyran-4-
      acetyl)
<220> FEATURE:
<221> NAME/KEY: MOD_RES
<222> LOCATION: (34)
<223> OTHER INFORMATION: AMIDATION

<400> SEQUENCE: 47
```

Ala Val Ser Glu His Gln Leu Leu His Asp Lys Gly Xaa Ser Ile Gln
 1               5                  10                  15

Asp Leu Arg Arg Arg Glu Leu Leu Glu Lys Leu Leu Glu Lys Leu His
                20                  25                  30

Thr Ala

```
<210> SEQ ID NO 48
<211> LENGTH: 35
<212> TYPE: PRT
<213> ORGANISM: Homo sapiens

<400> SEQUENCE: 48
```

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
                20                  25                  30

Thr Ala Gly
        35

```
<210> SEQ ID NO 49
<211> LENGTH: 33
<212> TYPE: PRT
<213> ORGANISM: Homo sapiens
<220> FEATURE:
<221> NAME/KEY: MOD_RES
<222> LOCATION: (4)
<223> OTHER INFORMATION: Glu(OCH3)
<220> FEATURE:
<221> NAME/KEY: MOD_RES
<222> LOCATION: (10)
<223> OTHER INFORMATION: Asp(OCH3)
<220> FEATURE:
<221> NAME/KEY: MOD_RES
<222> LOCATION: (17)
<223> OTHER INFORMATION: Asp(OCH3)
<220> FEATURE:
<221> NAME/KEY: MOD_RES
<222> LOCATION: (22)
<223> OTHER INFORMATION: Glu(OCH3)
<220> FEATURE:
<221> NAME/KEY: MOD_RES
<222> LOCATION: (25)
<223> OTHER INFORMATION: Glu(OCH3)
<220> FEATURE:
<221> NAME/KEY: MOD_RES
<222> LOCATION: (29)
<223> OTHER INFORMATION: Glu(OCH3)

<400> SEQUENCE: 49
```

Ala Val Ser Xaa His Gln Leu Leu His Xaa Lys Gly Lys Ser Ile Gln
 1               5                  10                  15

Xaa Leu Arg Arg Arg Xaa Leu Leu Xaa Lys Leu Leu Xaa Lys Leu His
                20                  25                  30

Ala

```
<210> SEQ ID NO 50
<211> LENGTH: 33
<212> TYPE: PRT
<213> ORGANISM: Homo sapiens
```

```
<220> FEATURE:
<221> NAME/KEY: MOD_RES
<222> LOCATION: (4)
<223> OTHER INFORMATION: Glu(OCH3)
<220> FEATURE:
<221> NAME/KEY: MOD_RES
<222> LOCATION: (10)
<223> OTHER INFORMATION: Asp(OCH3)
<220> FEATURE:
<221> NAME/KEY: MOD_RES
<222> LOCATION: (17)
<223> OTHER INFORMATION: Asp(OCH3)
<220> FEATURE:
<221> NAME/KEY: MOD_RES
<222> LOCATION: (22)
<223> OTHER INFORMATION: Glu(OCH3)
<220> FEATURE:
<221> NAME/KEY: MOD_RES
<222> LOCATION: (25)
<223> OTHER INFORMATION: Glu(OCH3)
<220> FEATURE:
<221> NAME/KEY: MOD_RES
<222> LOCATION: (29)
<223> OTHER INFORMATION: Glu(OCH3)
<220> FEATURE:
<221> NAME/KEY: MOD_RES
<222> LOCATION: (33)
<223> OTHER INFORMATION: -OCH3

<400> SEQUENCE: 50

Ala Val Ser Xaa His Gln Leu Leu His Xaa Lys Gly Lys Ser Ile Gln
 1               5                  10                  15

Xaa Leu Arg Arg Arg Xaa Leu Leu Xaa Lys Leu Leu Xaa Lys Leu His
                20                  25                  30

Ala

<210> SEQ ID NO 51
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: homoserine

<400> SEQUENCE: 51

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
                20                  25                  30

Thr Xaa

<210> SEQ ID NO 52
<211> LENGTH: 35
<212> TYPE: PRT
<213> ORGANISM: Homo sapiens

<400> SEQUENCE: 52

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
                20                  25                  30

Thr Ala Pro
            35

<210> SEQ ID NO 53
<211> LENGTH: 34
```

```
<212> TYPE: PRT
<213> ORGANISM: Homo sapiens

<400> SEQUENCE: 53
```

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
            20                  25                  30

Thr Pro

```
<210> SEQ ID NO 54
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 54
```

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
            20                  25                  30

Thr Pro

```
<210> SEQ ID NO 55
<211> LENGTH: 33
<212> TYPE: PRT
<213> ORGANISM: Homo sapiens
<220> FEATURE:
<221> NAME/KEY: MOD_RES
<222> LOCATION: (33)
<223> OTHER INFORMATION: AMIDATION

<400> SEQUENCE: 55
```

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
            20                  25                  30

Pro

```
<210> SEQ ID NO 56
<211> LENGTH: 32
<212> TYPE: PRT
<213> ORGANISM: Homo sapiens
<220> FEATURE:
<221> NAME/KEY: MOD_RES
<222> LOCATION: (32)
<223> OTHER INFORMATION: AMIDATION

<400> SEQUENCE: 56
```

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu Pro
            20                  25                  30

```
<210> SEQ ID NO 57
<211> LENGTH: 37
<212> TYPE: PRT
<213> ORGANISM: Homo sapiens

<400> SEQUENCE: 57
```

-continued

```
Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
                20                  25                  30

Thr Arg Ser Ala Trp
                35

<210> SEQ ID NO 58
<211> LENGTH: 42
<212> TYPE: PRT
<213> ORGANISM: Homo sapiens

<400> SEQUENCE: 58

Ala Val Ser Glu His Gln Leu Leu His Asp Arg Gly Arg Ser Ile Gln
 1               5                  10                  15

Asp Leu Arg Arg Arg Glu Leu Leu Glu Arg Leu Leu Glu Arg Leu His
                20                  25                  30

Thr Ala Gly Arg Arg Thr Arg Ser Ala Trp
                35                  40

<210> SEQ ID NO 59
<211> LENGTH: 42
<212> TYPE: PRT
<213> ORGANISM: Homo sapiens
<220> FEATURE:
<221> NAME/KEY: MOD_RES
<222> LOCATION: (42)
<223> OTHER INFORMATION: AMIDATION

<400> SEQUENCE: 59

Ala Val Ser Glu His Gln Leu Leu His Asp Arg Gly Arg Ser Ile Gln
 1               5                  10                  15

Asp Leu Arg Arg Arg Glu Leu Leu Glu Arg Leu Leu Glu Arg Leu His
                20                  25                  30

Thr Ala Gly Arg Arg Thr Arg Ser Ala Trp
                35                  40

<210> SEQ ID NO 60
<211> LENGTH: 42
<212> TYPE: PRT
<213> ORGANISM: Homo sapiens
<220> FEATURE:
<221> NAME/KEY: MOD_RES
<222> LOCATION: (12)
<223> OTHER INFORMATION: Lys(dihydrocinnamoyl)

<400> SEQUENCE: 60

Ala Val Ser Glu His Gln Leu Leu His Asp Arg Gly Xaa Ser Ile Gln
 1               5                  10                  15

Asp Leu Arg Arg Arg Glu Leu Leu Glu Arg Leu Leu Glu Arg Leu His
                20                  25                  30

Thr Ala Gly Arg Arg Thr Arg Ser Ala Trp
                35                  40

<210> SEQ ID NO 61
<211> LENGTH: 34
<212> TYPE: PRT
<213> ORGANISM: Homo sapiens
<220> FEATURE:
<221> NAME/KEY: MOD_RES
<222> LOCATION: (8)
<223> OTHER INFORMATION: Nle
<220> FEATURE:
<221> NAME/KEY: MOD_RES
```

```
<222> LOCATION: (18)
<223> OTHER INFORMATION: Nle
<220> FEATURE:
<221> NAME/KEY: MOD_RES
<222> LOCATION: (34)
<223> OTHER INFORMATION: AMIDATION

<400> SEQUENCE: 61

Ala Val Ser Glu Ile Gln Phe Xaa His Asn Leu Gly Lys His Leu Ser
 1               5                  10                  15

Ser Xaa Thr Arg Ser Ala Trp Leu Arg Lys Lys Leu Gln Asp Val His
            20                  25                  30

Asn Tyr

<210> SEQ ID NO 62
<211> LENGTH: 35
<212> TYPE: PRT
<213> ORGANISM: Homo sapiens
<220> FEATURE:
<221> NAME/KEY: MOD_RES
<222> LOCATION: (35)
<223> OTHER INFORMATION: AMIDATION

<400> SEQUENCE: 62

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
            20                  25                  30

Thr Met Ala
            35

<210> SEQ ID NO 63
<211> LENGTH:
<212> TYPE:
<213> ORGANISM:

<400> SEQUENCE: 63

This Sequence is intentionally skipped

<210> SEQ ID NO 64
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 64

Ala Val Ser Glu His Gln Leu Leu His Asp Lys Gly Lys Ser Ile Gln
 1               5                  10                  15

Asp Leu Arg Arg Arg Phe Phe Leu Glu Lys Leu Leu Glu Lys Leu His
            20                  25                  30

Thr Ala

<210> SEQ ID NO 65
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 65
```

```
Ala Val Ser Glu His Gln Leu Leu His Asp Lys Gly Lys Ser Ile Gln
 1               5                  10                  15

Asp Leu Arg Arg Arg Glu Leu Leu His Lys Leu Leu Glu Lys Leu His
                20                  25                  30

Thr Ala
```

<210> SEQ ID NO 66
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 66

```
Ala Val Ser Glu His Gln Leu Leu His Asp Lys Gly Lys Ser Ile Gln
 1               5                  10                  15

Asp Leu Arg Arg Arg Glu Leu Leu Glu His Leu Leu Glu Lys Leu His
                20                  25                  30

Thr Ala
```

<210> SEQ ID NO 67
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 67

```
Ala Val Ser Glu His Gln Leu Leu His Asp Lys Gly Lys Ser Ile Gln
 1               5                  10                  15

Asp Leu Arg Arg Arg Glu Leu Leu Glu Lys Leu Ile Ala Lys Leu His
                20                  25                  30

Thr Ala
```

<210> SEQ ID NO 68
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: AMIDATION

<400> SEQUENCE: 68

```
Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Glu Ile His
                20                  25                  30

Thr Ala
```

<210> SEQ ID NO 69
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: homoserine-NHCH2CH3

```
<400> SEQUENCE: 69

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
            20                  25                  30

Thr Xaa

<210> SEQ ID NO 70
<211> LENGTH: 34
<212> TYPE: PRT
<213> ORGANISM: Homo sapiens
<220> FEATURE:
<221> NAME/KEY: MOD_RES
<222> LOCATION: (34)
<223> OTHER INFORMATION: homoserine-NHCH2CH2C6H5

<400> SEQUENCE: 70

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
            20                  25                  30

Thr Xaa

<210> SEQ ID NO 71
<211> LENGTH:
<212> TYPE:
<213> ORGANISM:

<400> SEQUENCE: 71

This Sequence is intentionally skipped

<210> SEQ ID NO 72
<211> LENGTH: 37
<212> TYPE: PRT
<213> ORGANISM: Homo sapiens
<220> FEATURE:
<221> NAME/KEY: MOD_RES
<222> LOCATION: (37)
<223> OTHER INFORMATION: AMIDATION

<400> SEQUENCE: 72

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
            20                  25                  30

Thr Arg Ser Ala Trp
            35

<210> SEQ ID NO 73
<211> LENGTH: 37
<212> TYPE: PRT
<213> ORGANISM: Homo sapiens
<220> FEATURE:
<221> NAME/KEY: MOD_RES
<222> LOCATION: (37)
<223> OTHER INFORMATION: 3-(2-naphthyl)-L-alanine

<400> SEQUENCE: 73

Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
            20                  25                  30
```

-continued

Thr Arg Ser Ala Xaa
            35

<210> SEQ ID NO 74
<211> LENGTH: 37
<212> TYPE: PRT
<213> ORGANISM: Homo sapiens

<400> SEQUENCE: 74

Ala Val Ser Glu His Gln Leu Leu His Asp Lys Gly Lys Ser Ile Gln
  1               5                  10                  15

Asp Leu Arg Arg Arg Glu Leu Leu Glu Lys Leu Leu Glu Lys Leu His
             20                  25                  30

Thr Ala Ser Ala Trp
            35

<210> SEQ ID NO 75
<211> LENGTH: 38
<212> TYPE: PRT
<213> ORGANISM: Homo sapiens

<400> SEQUENCE: 75

Ala Val Ser Glu His Gln Leu Leu His Asp Lys Gly Lys Ser Ile Gln
  1               5                  10                  15

Asp Leu Arg Arg Arg Glu Leu Leu Glu Lys Leu Leu Glu Lys Leu His
             20                  25                  30

Thr Ala Glu Ile Arg Ala
            35

<210> SEQ ID NO 76
<211> LENGTH: 37
<212> TYPE: PRT
<213> ORGANISM: Homo sapiens

<400> SEQUENCE: 76

Ala Val Ser Glu His Gln Leu Leu His Asp Lys Gly Lys Ser Ile Gln
  1               5                  10                  15

Asp Leu Arg Arg Arg Glu Leu Leu Glu Lys Leu Leu Glu Lys Leu His
             20                  25                  30

Thr Ala Glu Ile Arg
            35

<210> SEQ ID NO 77
<211> LENGTH: 36
<212> TYPE: PRT
<213> ORGANISM: Homo sapiens

<400> SEQUENCE: 77

Ala Val Ser Glu His Gln Leu Leu His Asp Lys Gly Lys Ser Ile Gln
  1               5                  10                  15

Asp Leu Arg Arg Arg Glu Leu Leu Glu Lys Leu Leu Glu Lys Leu His
             20                  25                  30

Thr Ala Glu Ile
            35

<210> SEQ ID NO 78
<211> LENGTH: 35
<212> TYPE: PRT
<213> ORGANISM: Homo sapiens

<400> SEQUENCE: 78

-continued

```
Ala Val Ser Glu His Gln Leu Leu His Asp Lys Gly Lys Ser Ile Gln
 1               5                  10                  15

Asp Leu Arg Arg Arg Glu Leu Leu Glu Lys Leu Leu Glu Lys Leu His
            20                  25                  30

Thr Ala Glu
         35
```

<210> SEQ ID NO 79
<211> LENGTH: 34
<212> TYPE: PRT
<213> ORGANISM: Homo sapiens
<220> FEATURE:
<221> NAME/KEY: MOD_RES
<222> LOCATION: (8)
<223> OTHER INFORMATION: Nle
<220> FEATURE:
<221> NAME/KEY: MOD_RES
<222> LOCATION: (18)
<223> OTHER INFORMATION: Nle
<220> FEATURE:
<221> NAME/KEY: MOD_RES
<222> LOCATION: (34)
<223> OTHER INFORMATION: homoserinelactone

<400> SEQUENCE: 79

```
Ala Val Ser Glu Ile Gln Phe Xaa His Asn Lys Gly Lys His Leu Ser
 1               5                  10                  15

Ser Xaa Glu Arg Val Glu Trp Leu Arg Lys Lys Leu Gln Asp Val His
            20                  25                  30

Asn Xaa
```

<210> SEQ ID NO 80
<211> LENGTH: 32
<212> TYPE: PRT
<213> ORGANISM: Homo sapiens
<220> FEATURE:
<221> NAME/KEY: MOD_RES
<222> LOCATION: (32)
<223> OTHER INFORMATION: AMIDATION

<400> SEQUENCE: 80

```
Ser Glu His Gln Leu Leu His Asp Lys Gly Lys Ser Ile Gln Asp Leu
 1               5                  10                  15

Arg Arg Arg Glu Leu Leu Glu Lys Leu Leu Glu Lys Leu His Thr Ala
            20                  25                  30
```

<210> SEQ ID NO 81
<211> LENGTH: 28
<212> TYPE: PRT
<213> ORGANISM: Homo sapiens
<220> FEATURE:
<221> NAME/KEY: MOD_RES
<222> LOCATION: (28)
<223> OTHER INFORMATION: AMIDATION

<400> SEQUENCE: 81

```
Leu Leu His Asp Lys Gly Lys Ser Ile Gln Asp Leu Arg Arg Arg Glu
 1               5                  10                  15

Leu Leu Glu Lys Leu Leu Glu Lys Leu His Thr Ala
            20                  25
```

<210> SEQ ID NO 82
<211> LENGTH: 28
<212> TYPE: PRT
<213> ORGANISM: Homo sapiens
<220> FEATURE:

```
<221> NAME/KEY: MOD_RES
<222> LOCATION: (28)
<223> OTHER INFORMATION: AMIDATION

<400> SEQUENCE: 82

Leu Leu His Asp Lys Gly Lys Ser Ile Gln Asp Leu Arg Arg Arg Glu
 1               5                  10                  15
Leu Leu Glu Lys Leu Leu Glu Lys Leu His Thr Ala
            20                  25

<210> SEQ ID NO 83
<211> LENGTH: 39
<212> TYPE: PRT
<213> ORGANISM: Homo sapiens

<400> SEQUENCE: 83

Ser Glu His Gln Leu Leu His Asp Arg Gly Arg Ser Ile Gln Asp Leu
 1               5                  10                  15
Arg Arg Arg Glu Leu Leu Glu Arg Leu Leu Glu Arg Leu His Ala Gly
            20                  25                  30
Arg Arg Thr Arg Ser Ala Trp
        35

<210> SEQ ID NO 84
<211> LENGTH: 35
<212> TYPE: PRT
<213> ORGANISM: Homo sapiens

<400> SEQUENCE: 84

Leu Leu His Asp Arg Gly Arg Ser Ile Gln Asp Leu Arg Arg Arg Glu
 1               5                  10                  15
Leu Leu Glu Arg Leu Leu Glu Arg Leu His Ala Gly Arg Arg Thr Arg
            20                  25                  30
Ser Ala Trp
        35

<210> SEQ ID NO 85
<211> LENGTH: 10
<212> TYPE: PRT
<213> ORGANISM: Homo sapiens
<220> FEATURE:
<221> NAME/KEY: MOD_RES
<222> LOCATION: (1)
<223> OTHER INFORMATION: Glu, Glu(OCH3), His or Phe
<220> FEATURE:
<221> NAME/KEY: MOD_RES
<222> LOCATION: (2)
<223> OTHER INFORMATION: Leu or Phe
<220> FEATURE:
<221> NAME/KEY: MOD_RES
<222> LOCATION: (4)
<223> OTHER INFORMATION: Glu, Glu(OCH3), His or Phe
<220> FEATURE:
<221> NAME/KEY: MOD_RES
<222> LOCATION: (5)
<223> OTHER INFORMATION: Lys or His
<220> FEATURE:
<221> NAME/KEY: MOD_RES
<222> LOCATION: (7)
<223> OTHER INFORMATION: Leu or Ile
<220> FEATURE:
<221> NAME/KEY: MOD_RES
<222> LOCATION: (8)
<223> OTHER INFORMATION: Ala, Arg or Glu
<220> FEATURE:
<221> NAME/KEY: MOD_RES
<222> LOCATION: (9)
<223> OTHER INFORMATION: Lys or Glu
```

```
-continued

<220> FEATURE:
<221> NAME/KEY: MOD_RES
<222> LOCATION: (10)
<223> OTHER INFORMATION: Leu or Ile

<400> SEQUENCE: 85

Xaa Xaa Leu Xaa Xaa Leu Xaa Xaa Xaa Xaa
 1               5                  10

<210> SEQ ID NO 86
<211> LENGTH: 10
<212> TYPE: PRT
<213> ORGANISM: Homo sapiens
<220> FEATURE:
<221> NAME/KEY: MOD_RES
<222> LOCATION: (1)
<223> OTHER INFORMATION: Glu, Glu(OCH3), His or Phe
<220> FEATURE:
<221> NAME/KEY: MOD_RES
<222> LOCATION: (2)
<223> OTHER INFORMATION: Leu or Phe
<220> FEATURE:
<221> NAME/KEY: MOD_RES
<222> LOCATION: (4)
<223> OTHER INFORMATION: Glu, Glu(OCH3), His or Phe
<220> FEATURE:
<221> NAME/KEY: MOD_RES
<222> LOCATION: (8)
<223> OTHER INFORMATION: Glu or Lys

<400> SEQUENCE: 86

Xaa Xaa Leu Xaa Arg Leu Leu Xaa Arg Leu
 1               5                  10

<210> SEQ ID NO 87
<211> LENGTH: 12
<212> TYPE: PRT
<213> ORGANISM: Homo sapiens

<400> SEQUENCE: 87

Ala Val Ser Glu His Gln Leu Leu His Asp Lys Gly
 1               5                  10

<210> SEQ ID NO 88
<211> LENGTH: 11
<212> TYPE: PRT
<213> ORGANISM: Homo sapiens

<400> SEQUENCE: 88

Lys Ser Ile Gln Asp Leu Arg Arg Arg Glu Leu
 1               5                  10

<210> SEQ ID NO 89
<211> LENGTH: 11
<212> TYPE: PRT
<213> ORGANISM: Homo sapiens

<400> SEQUENCE: 89

Leu Glu Lys Leu Leu Glu Lys Leu His Thr Ala
 1               5                  10

<210> SEQ ID NO 90
<211> LENGTH: 10
<212> TYPE: PRT
<213> ORGANISM: Homo sapiens

<400> SEQUENCE: 90

Lys Ser Ile Gln Asp Leu Arg Arg Arg Glu
```

```
<210> SEQ ID NO 91
<211> LENGTH: 12
<212> TYPE: PRT
<213> ORGANISM: Homo sapiens

<400> SEQUENCE: 91

Leu Leu Glu Lys Leu Leu Glu Lys Leu His Thr Ala
 1               5                  10
```